United States Patent
Borden et al.

(10) Patent No.: US 9,820,643 B2
(45) Date of Patent: Nov. 21, 2017

(54) ILLUMINATION EVALUATION OR RECOMMENDATION USING VISUAL FUNCTION

(71) Applicant: Jasper Ridge Inc., Menlo Park, CA (US)

(72) Inventors: Peter Gustave Borden, San Mateo, CA (US); Michele Klein, Portola Valley, CA (US)

(73) Assignee: Jasper Ridge Inc., Menlo Park, CA (US)

( * ) Notice: Subject to any disclaimer, the term of this patent is extended or adjusted under 35 U.S.C. 154(b) by 0 days.

(21) Appl. No.: 15/043,767

(22) Filed: Feb. 15, 2016

(65) Prior Publication Data

US 2016/0157712 A1 Jun. 9, 2016

Related U.S. Application Data

(63) Continuation-in-part of application No. PCT/US2014/050738, filed on Aug. 12, 2014.

(Continued)

(51) Int. Cl.
*A61B 3/02* (2006.01)
*A61B 3/14* (2006.01)
(Continued)

(52) U.S. Cl.
CPC .............. *A61B 3/063* (2013.01); *A61B 3/005* (2013.01); *A61B 3/0008* (2013.01); *A61B 3/0033* (2013.01)

(58) Field of Classification Search
CPC ....... A61B 3/024; A61B 3/032; A61B 3/1225; A61B 3/02; A61B 3/18; A61B 3/1015;
(Continued)

(56) References Cited

U.S. PATENT DOCUMENTS

| 2,795,993 A | 6/1957 | Leverett et al. |
| 5,121,981 A | 6/1992 | Waltuck et al. |

(Continued)

FOREIGN PATENT DOCUMENTS

| CN | 103604584 A | 2/2014 |
| DE | 19731082 A1 | 1/1999 |

(Continued)

OTHER PUBLICATIONS

"International Application Serial No. PCT/US2014/050738, International Preliminary Report on Patentability dated Feb. 25, 2016", 14 pgs.

(Continued)

*Primary Examiner* — Dawayne A Pinkney
(74) *Attorney, Agent, or Firm* — Schwegman Lundberg & Woessner, P.A.

(57) ABSTRACT

Illumination can be evaluated for patient using a system including a housing, an adjustable light source mechanically coupled to the housing and configured to illuminate an object for viewing by the patient on an axis substantially perpendicular to a surface of the object. A user-adjustable input coupled to the adjustable light source is to obtain information from a user indicative of a calibrated illuminance and a color property to be provided by the adjustable light source including providing a range of adjustable illuminance and color properties selectable by the user. The adjustable light source can be configured to provide light having an illuminance in excess of 300 lux, and the housing can be configured to provide a first specified distance between the adjustable light source and the object for viewing and to obstruct viewing of the light source directly by the patient.

33 Claims, 10 Drawing Sheets

Related U.S. Application Data

(60) Provisional application No. 61/865,563, filed on Aug. 13, 2013, provisional application No. 61/883,380, filed on Sep. 27, 2013, provisional application No. 61/891,406, filed on Oct. 16, 2013, provisional application No. 61/921,625, filed on Dec. 30, 2013, provisional application No. 61/933,282, filed on Jan. 29, 2014, provisional application No. 62/000,707, filed on May 20, 2014, provisional application No. 62/118,427, filed on Feb. 19, 2015, provisional application No. 62/146,870, filed on Apr. 13, 2015.

(51) Int. Cl.
*A61B 3/00* (2006.01)
*A61B 3/06* (2006.01)

(58) Field of Classification Search
CPC .. A61B 3/103; A61B 3/08; A61B 3/14; A61B 3/113; A61H 5/00
USPC ........ 351/221–223, 243–246, 200–201, 203, 351/205–206, 209–211
See application file for complete search history.

(56) References Cited

U.S. PATENT DOCUMENTS

| | | | |
|---|---|---|---|
| 5,550,602 A | 8/1996 | Braeuning | |
| 5,883,694 A | 3/1999 | Mumford | |
| 7,204,591 B2 | 4/2007 | Wertheim et al. | |
| 7,380,940 B2 | 6/2008 | Anderson et al. | |
| 8,016,420 B2 | 9/2011 | Yee et al. | |
| 8,132,916 B2 | 3/2012 | Johansson | |
| 8,764,188 B2* | 7/2014 | Tabor | A61B 3/08 351/201 |
| 2002/0171373 A1* | 11/2002 | Muthu | G01J 3/51 315/219 |
| 2011/0089830 A1 | 4/2011 | Pickard et al. | |
| 2012/0306381 A1 | 12/2012 | Adler | |
| 2013/0176534 A1 | 7/2013 | Frankfort et al. | |
| 2013/0194317 A1 | 8/2013 | Guillon et al. | |
| 2014/0221868 A1* | 8/2014 | Mulheran | A61B 5/128 600/558 |

FOREIGN PATENT DOCUMENTS

| | | |
|---|---|---|
| JP | 2007068925 A | 3/2007 |
| KR | 101019468 B1 | 11/2010 |
| WO | WO-2008064379 A1 | 6/2008 |
| WO | WO-2011043922 A1 | 4/2011 |
| WO | WO-2011163672 A2 | 12/2011 |
| WO | WO-2015023676 A1 | 2/2015 |

OTHER PUBLICATIONS

"International Application Serial No. PCT/US2014/050738, International Search Report dated Dec. 1, 2014", 2 pgs.

"International Application Serial No. PCT/US2014/050738, Written Opinion dated Dec. 1, 2014", 12 pgs.

"LED 3Colour Lamp for Assessment", (May 31, 2014), 2 pgs.

"LED Technology—Innovation for Visual Color Evaluation", [Online]. Retrieved from the Internet: <URL: www.konicaminolta.eu, (May 2012), 4 pgs.

Bowers, Alex R., et al., "Illumination and reading performance in age-related macular degeneration", Clin Exp Optom 84: 3, (2001), 139-147.

Legge, Gordon E., "Psychophysics of Reading in Normal and Low Visiion", Chapter 4, (2007), p. 162.

* cited by examiner

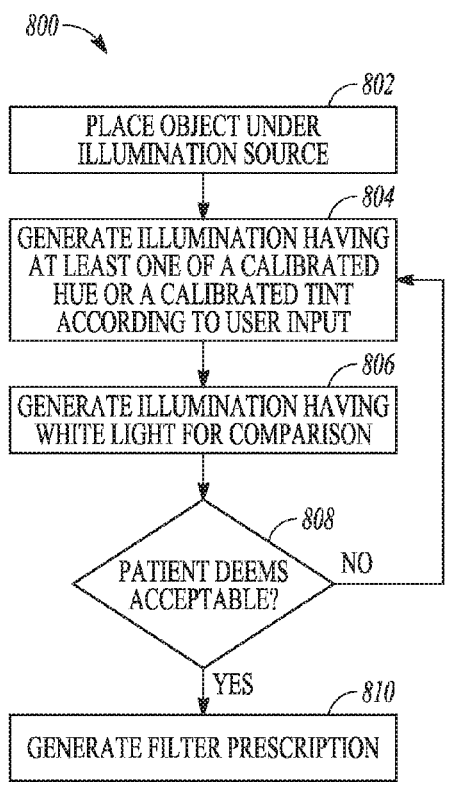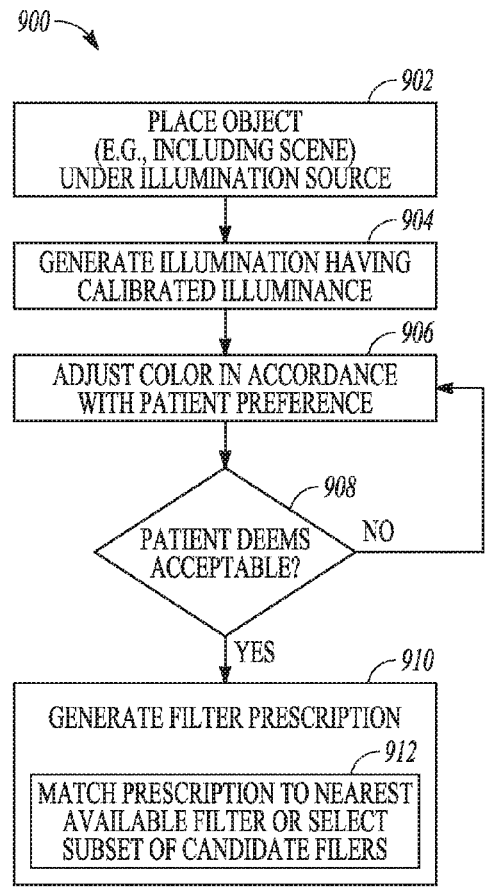
FIG. 8
FIG. 9

ILLUMINATION EVALUATION OR RECOMMENDATION USING VISUAL FUNCTION

CLAIM OF PRIORITY

This application is a continuation-in-part under 35 U.S.C. 111(a) of International Application No. PCT/US2014/050738, filed Aug. 12, 2014, and published on Feb. 19, 2015 as WO 2015/023676 A1, titled "ILLUMINATION EVALUATION OR RECOMMENDATION USING VISUAL FUNCTION,", which claimed benefit of priority of each of (1) U.S. Provisional Patent Application Ser. No. 61/865,563, titled "A device for visual acuity versus illuminance," filed on Aug. 13, 2013, (2) U.S. Provisional Patent Application Ser. No. 61/883,380, titled "A device for measuring reading acuity versus illuminance and color," filed on Sep. 27, 2013, (3) U.S. Provisional Patent Application Ser. No. 61/921,625, titled "Software to recommend optimum lighting," filed on Dec. 30, 2013, (4) U.S. Provisional Patent Application Ser. No. 61/891,406, titled "Software to recommend optimum lighting," filed on Oct. 16, 2013, (5) U.S. Provisional Patent Application Ser. No. 61/933,282, titled "A system and method to choose commercial task lighting," filed on Jan. 29, 2014, and (6) U.S. Provisional Patent Application Ser. No. 62/000,707, titled "A system and method to determine the optimum color for tinted lenses," filed on May 20, 2014, the benefit of each of which is hereby presently claimed, and each of which is incorporated by reference herein in its entirety; and this application also claims benefit of priority of (7) U.S. Provisional Patent Application Ser. No. 62/118,427, titled "A system and method to determine optimum lens tints and demonstrate the effect to a patient," filed Feb. 19, 2015, and (8) U.S. Provisional Patent Application Ser. No. 62/146,870, titled "A system and method for assessing tinted lenses to improve safety," filed Apr. 13, 2015, the benefit of each of which is hereby presently claimed, and each of which is incorporated by reference herein in its entirety.

BACKGROUND

Bright light is a clinical intervention that can help people with chronic eye diseases such as macular degeneration recover lost visual function. For example, a study showed that among the 89% with macular degeneration, the average gain in reading acuity was greater than 0.2 log MAR (corresponding to the ability to read about 60% smaller letter size) when illuminance was increased from 125 lumens per square meter (lux) to 2050 lux. 125 lux is a lighting level that can be found in a typical home. However, many patients may achieve full acuity at 1500-2000 lux, and some may need over 5000 lux to achieve acuity.

Clinicians can test for response to increased lighting, but these tests are generally not controlled. For example, a patient's reading acuity may be evaluated using standard charts such as the MN read or SK read using ambient examining room light. The patient can then tested while wearing 4% transmission sunglasses. The assumption is generally that if reading acuity drops with the sunglasses (reduced light), then reading acuity would increase with bright light. However, this assumption may be inaccurate, for example, because increased light often introduces glare. Also, perceived brightness is generally non-linear, so the actual benefit from increased light may be smaller than assumed on the basis of the loss from reduced light.

In other cases, the doctor may employ a desk lamp to test for the benefit of brighter illuminance. However, such sources are rarely calibrated, and the illuminance is a sensitive function of their position with respect to the reading material or vision chart, so such testing is generally not repeatable. Also, a non-linear response of the eye may erroneously indicate less benefit at intermediate levels of illuminance than would actually be realized if testing were performed with a very bright light source. A test in the office with bright light can also be confounded by glare, from reflections off the eye chart or from sources such as a poorly positioned lamp. In such an examination environment, it can be difficult to control factors to obtain reproducible results, including glare, intensity and light uniformity at the plane of the chart.

An additional problem is that there is no standard method for converting the result of a lighting assessment into a recommendation for a lamp or light bulb that can produce the optimum lighting condition found in the exam, so the patient can duplicate the lighting at home, work or school. Without an existing technique to offer this recommendation, the assessment itself is of limited practical value to the patient.

Color and color temperature can also play a role in eye strain and comfort in reading, and are factors that can be considered in selecting lighting. Color, or tints of glasses can also play an important role in outdoor vision performance. Accordingly, a problem exists because no standard test device or technique exists to determine a patient response to increased illuminance including providing reproducible test conditions and control of factors that can influence results, allows for testing with different colors of light, and has a quantified output that can be entered into a medical record, and no technique or system for the clinician to offer a recommendation on how the patient can duplicate ideal lighting conditions after leaving the office.

OVERVIEW

The present inventors have recognized, among other things, that it is desirable for clinicians to have a simple, fast, and calibrated technique to quantify a patient response to increased lighting. Near visual performance (e.g., a reading performance) of a patient can be improved through magnification or adjustment of light intensity. Optometrists generally obtain a quantitative measure of refraction (the lens power to provide optimum magnification and correction), and then prescribe lens parameters based on the quantitative measurement. The prescription can then be dispensed as one or more corrective lenses. However, the present inventors have recognized that in the domain of lighting there are generally no standardized apparatus or techniques in an eye exam to obtain a quantitative measurement of light intensity and color that enhances patient visual performance, and then provides a prescription based on that quantitative measurement, so that lighting based on the prescription can then be "dispensed" either via physically providing a lighting device meeting the prescribed criteria or virtually through providing a lighting recommendation that can include identifying a specific lighting product for purchase. Here, visual performance includes factors such as acuity and reduction in eye strain. For example, improved performance could indicate the ability to read smaller lines on an eye chart, to read for a longer duration because of reduced eye strain, or both.

Because of the wide range of available lighting devices and fixtures—sometimes having inconsistent or inaccurate specifications—it can be difficult to select a lighting product that best matches an individual's lighting needs. This difficulty can be further compounded when a patient suffers from a chronic eye condition such as macular degeneration, or even aging. In such cases, the individual may need very high levels of illuminance and minimized glare.

This prescription can be specified, for example, in terms of units of illuminance, such as lux or foot-candles (or luminance, which can be directly related to illuminance such as by considering a reflectance of the page). The prescription can also be specified in terms of a color property such as a color temperature. Color temperature can be identified, such as in degrees Kelvin (or, for colored light, a wavelength or color such as, e.g., green, blue, yellow, red, or another color, or a tint, which is a mixture of white and colored light).

In an example, a system can be used to evaluate illumination for a patient, the system including a housing, an adjustable light source mechanically coupled to the housing and configured to illuminate an object for viewing by the patient on an axis substantially perpendicular to a surface of the object, a user-adjustable input coupled to the adjustable light source, the user-adjustable input configured to obtain information from a user indicative of a calibrated illuminance and a color property to be provided by the adjustable light source including providing a range of adjustable illuminance and color properties selectable by the user, and an indicator configured to provide indicia of a selected illuminance and a selected color property to the user. The adjustable light source can be configured to provide light having an illuminance in excess of 300 lux, and the housing can be configured to provide a first specified distance between the adjustable light source and the object for viewing and to obstruct viewing of the light source directly by the patient. The calibrated illuminance can be established at least in part using the specified distance provided by the housing.

A prescription specified in terms of one or more of illuminance or color property, such as provided by the system above, may still not be easily related to commercially-available lighting devices or fixtures. Therefore, the present inventors have also recognized that a lighting prescription can be further related to, or used to provide, a lighting recommendation, such as including at least one of a recommended lighting technology, a recommended lighting distance, a recommended color property, a recommended lumen output, a recommended wattage, or a recommended lighting fixture that meets the specifications of the prescription.

In an example, using a prescription, a recommendation for a specific lighting product can be provided, such as using information about at least one of the recommended lighting technology, the recommended lighting distance, the recommended color property, the recommended lumen output, the recommended wattage, or the recommended lighting fixture. For example, such as using a web-based portal or a database communicatively coupled to a tablet, desktop, or mobile device, a specific lighting product recommendation can be generated (or multiple such recommendations can be provided), such as including information about at least one of a lighting manufacturer, a lighting vendor, a product identification, or a price. For example, information about a geographic location of a patient or caregiver can be used, so that specific lighting product recommendations can be made such as using information tailored to include channel partners (e.g., nearby hardware stores, home improvement stores, or online retailers).

In another example, the apparatus and techniques described herein can be used to assist in selecting appropriate color properties (e.g., hue and tint) for tinted lenses. Vision clinicians often prescribe tinted lenses for patients having glasses or contacts. While these are in some cases cosmetic, if selected appropriately such tinted lenses can reduce eye strain and give a perception of improved contrast. Such factors can be important for near vision, especially when the patient is performing long duration tasks such as reading or fine work. Many tinted glasses have enhanced transmission in certain wavelength bands so they appear to have a certain color, such as pink, green or yellow, while others (such as grey or brown) are neutral density, and have a relatively flat transmission across the visible spectrum. It can be difficult and time consuming to determine the optimum color for tinted lenses, as such determination generally involves fitting and exchanging several pairs of glasses. This manual selection process also generally involves the patient being asked to remember how one tint looks when trying another. Tinted lenses are also worn outdoors, but it is generally difficult to assess the best tint if the patient is indoors in an exam room.

The present inventors have also recognized that the apparatus and techniques described herein can be used to provide a rapid method to determine one or more color properties to aid in selecting a commercially available lens that provides better or best vision performance for a patient. In an example, a system can be used to evaluate a color property for a lens for a patient by using adjustable illumination to emulate the color property of a prescribed lens, the system including a housing, an adjustable light source mechanically coupled to the housing and configured to illuminate an object for viewing by the patient on an axis substantially perpendicular to a surface of the object, a user-adjustable input coupled to the adjustable light source, the user-adjustable input configured to obtain information from a user indicative of a hue and a tint to be provided by the adjustable light source including providing a range of adjustable hue and tint values selectable by the user, and an indicator configured to provide indicia of a selected hue and a selected tint to the user. The adjustable light source can be configured to provide light having an illuminance in excess of 300 lux and the housing can be configured to provide a first specified distance between the adjustable light source and the object for viewing, and to obstruct viewing of the light source directly by the patient.

The present inventors have also recognized that a combination of light sources can be used such as for determining a tinted lens prescription, such as including a combination of white light sources (such as having color temperatures of selected from a range of about 2,700° K to about 6,500° K) and colored light sources (e.g., red and green light sources), such as can be used to simulate a "blue blocker" filter. In an example, the colored light sources can include red, green, and blue sources, such as interspersed in a linear or areal array along with one or more white sources. In an example, the present inventors have recognized that an object illuminated by one or more light sources for evaluation can include a picture of a scene indicative of an environment in which the patient will use a prescribed tinted lens. The scene can include a photograph or other medium, such as having a printed color rendering having a modified tint (e.g., green or brown tint) to assist in evaluating a particular tint prescription along with use of calibrated illumination.

The present inventors have also recognized that the apparatus and techniques described herein can be used to provide a rapid method to evaluate a presence or degree of traumatic brain injury (TBI), such as can be determined quantitatively using a change in color preference when evaluating light sensitivity.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIGS. 5A through 5C illustrate generally illustrative examples of user interfaces that can be used to one or more of present information to a user such as for providing a lighting recommendation, or receive input from the user.

FIG. 8 illustrates generally a technique, such as a method, that can include generating illumination having at least one of a calibrated hue or a calibrated tint according to a user input, including generating illumination having white light for comparison.

FIG. 9 illustrates generally a technique, such as a method, that can include placing an object depicting a scene under an illumination source, including generating illumination having a calibrated illuminance.

DETAILED DESCRIPTION

Figure 1:
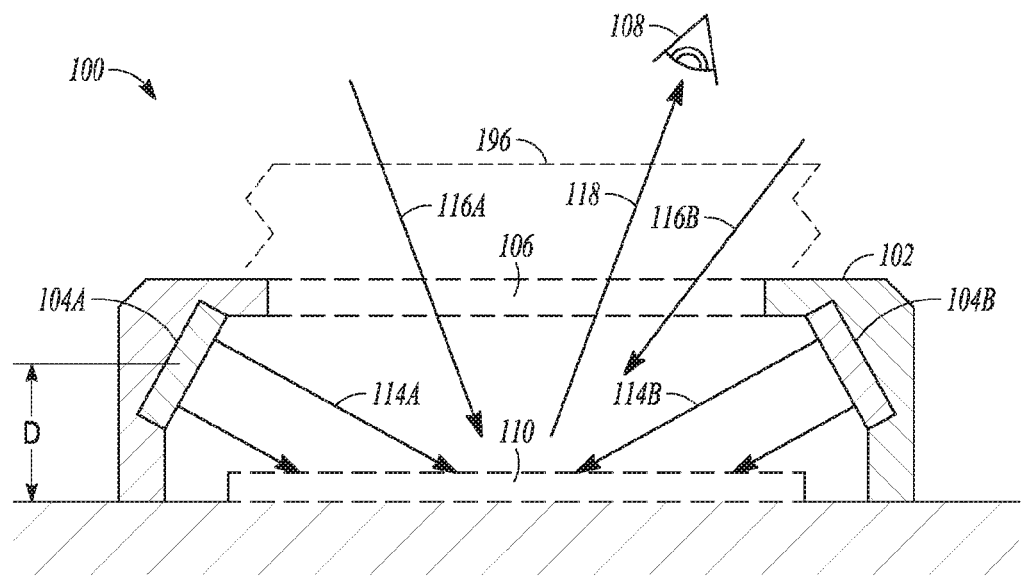
FIG. 1 illustrates generally an example of a side section view of at least a portion of an apparatus, such as for evaluating visual acuity.

FIG. 1 illustrates generally an example of a side section view of at least a portion of an apparatus 100, such as for evaluating visual acuity. In the example of FIG. 1, one or more adjustable light sources such as a first light source 104A or second light source 104B can be located on or within a housing 102 and mechanically coupled to the housing 102, such as to provide adjustable illumination 114A or 114B of an object 110. The illumination 114A or 114B can be along an axis or a range of angles that are predominantly or entirely non-parallel and non-perpendicular to a surface of the object 110. The housing 102 can be configured to include an aperture 106, such as to permit viewing of the illuminated object 110 by a patient 108 or other user. Ambient illumination 116A or 116B can also illuminate the object 110, such as to assist in providing a realistic combination of ambient diffuse light along with adjustable intense light that can be provided by the first or second adjustable light sources 104A or 104B. The housing 102 and light sources 104A and 104B can be arranged to provide a precise, repeatable, specified distance, "D," between the light sources 104A and 104B, and the object 110, unlike other approaches where a free-standing lamp is used. In this manner, the illuminance provided by the adjustable light sources 104A and 104B can be calibrated, without user adjustment. The adjustable light sources 104A or 104B can include light-emitting diodes (LEDs), such as each including a bar or other array configuration of LEDs. The housing 102 can include other circuitry, such as drive electronics or a processor circuit, as discussed in other examples below, such as to receive a user input and provide one or more of a calibrated illuminance or a desired color property, using the adjustable light sources 104A or 104B. The adjustable light sources 104A and 104B can be arranged symmetrically, such as shown in the illustration of FIG. 1.

In an example, such as shown in FIG. 1, the adjustable light sources 104A or 104B can be obstructed at least in part by the housing 102, such as to prevent the patient 108 from being dazzled or otherwise distracted by direct light emission from the sources rather than reflection 118 of the light off the surface of the object 110 being viewed. As discussed in other examples, a range of adjustable calibrated illuminance values or one or more color properties can be rapidly evaluated and one or more of a calibrated illuminance or a color property can be identified as more or most beneficial for viewing of the object 110 by the user. The identified calibrated illuminance or color property can be provided as a lighting prescription, and can be further used to automatically determine specific lighting recommendations, such as used for identifying a specific lighting product for purchase or use by the patient. In an illustrative example, a vertical distance from the object 110 to the centerline of the light source 104A and 104B (e.g., diode arrays) is 35 mm. In this illustrative example, the aperture 106 length is 72 mm and width 180 mm. The light sources 104A and 104B include diode arrays recessed 25 mm from the aperture 106 and mounted at a downward facing angle of 20 degrees. Each diode array includes 24 LEDs with a center-to-center spacing of 6 mm. The LEDs are in six repeating groups of four, in a sequence of cold white (Cree MLEAWT-A1-0000-0004E1), green (Cree MLEGRN-A1-0000-000002), warm white (Cree MLCAWT-A1-8B1-K2-0-00009), and red (Cree MLERED-A1-0000-000V03). The six LEDs of each color type are wired in series in this illustrative example.

The apparatus 100 shown in FIG. 1 can be used to reproducibly evaluate and document a measure of the effect of varied illumination or varied color property (e.g., hue or color temperature) while controlling such effects that can skew such measurements, such as glare, variation of a distance between an illuminated object 110 and the light source, or a lack of illuminance calibration or non-uniformity. It is additionally possible to either include ambient light, which is important in a home lighting assessment, or to eliminate such effects by dimming the ambient lighting. Furthermore, the evaluation can be performed using a variety of different common eye charts, such as ETDRS, tumbling E, MN Read, SK Read, Pelli-Robson, Colenbrander mixed contrast, IReST, or one or more other charts. The object 110 need not be an eye chart, and can include a printed matter such as a magazine, newspaper, representative restaurant menu, or other subject matter, such as an excerpt mounted or printed on a card to facilitate re-use. The object 110 can include a black-and-white or color image, to simulate an outdoor scene in, for example, an examination in a clinic. When illuminating the image with tinted or colored light, this is of value in determining the effect of tinted glasses without having to take the patient outdoors. In an example, an electronic display can be used for the object 110, such as an e-ink display or other display corresponding to an e-book or other device. Generally, the apparatus 100 can be more effective in evaluating the benefit of increased illumination when reflective media is used for the object 110, so the object 110 would generally include printed material or a reflective-type electronic display rather than an emissive display if an electronic display 110 is used for the object 110.

Generally, a plane of a surface of the object 110 is substantially perpendicular (e.g., normal) to an axis of viewing by the patient 108. In an example, one or more of the housing 102 or the object 110 can be tilted to reduce or eliminate direct reflection to the subject's eyes (minimizing specular, as opposed to the diffuse reflection expected from the matte surface of an eye chart with illumination angles far from the perpendicular (e.g., normal) axis). In an example, subject matter of the object 110 (e.g., a chart) can be key-stoned (e.g., as with a projector), such as to correct for distortion due to tilting or off-axis viewing.

The housing 102 can include interior or exterior baffling or light absorbing layers such as can include matte black paint or felt, such as to suppress reflection of light. For example, baffling can include a section that recesses the light sources and black walls to block light that would otherwise find a path to the subject's eyes. In another example, one or more of the inner walls of the light source can include diffuse reflective surfaces (a diffuse reflector can be similar to a white matte surface, versus a specular reflective surface which can be similar to a mirror), such as in order to increase uniformity of illuminance. For example, interior walls of the housing 102 or light sources 104A or 104B can be tilted or recessed so they are not visible through the aperture 106. According to an illustrative example, the aperture 106 can be an 18 centimeter (cm)×7.2 cm rectangle, such as having the 18 cm long axis oriented parallel with the adjustable light sources 104A or 104B, such as when the adjustable light sources include LED "bar" arrays. In some embodiments, the housing 102 does not admit a significant amount of room light 116A or 116B, lest the room light interfere with the calibration or cause glare. For example, a material used for the housing 102 can be opaque or coated to suppress transmission of light through the housing 102. For example, the housing can be fabricated using a dyed or non-transmissive material as black or smoky-colored plastic that has small or negligible transmission, for example allowing transmission of less than 10% of the ambient light. This can allow a person conducting the exam to see the position of the light source on the eye chart lines as the patient 108 views them.

In another example, some parts of the housing 102 are opaque and some partially or completely transmit light. For example, the housing 102 can include at least one window outside of the aperture 106 area, through which the object 110 can be viewed by the clinician, such as to allow the clinician to identify which line on the object 110 is being read (e.g., an eye chart).

Maintaining a specified distance between the patient 108 and the object 110 can also help to provide a reproducible measurement. In an example, the patient reads at their most comfortable distance, which may be determined by their vision correction. In another example, a spacer 196 can be used between the patient 108 and the housing 102, such as to maintain a specified distance between the patient 108 and the housing 102. For example, a spacer 196 can include a fixed tube and can have a specified length, such as 10 cm, 20 cm, 40 cm or 1 meter. The spacer 196 can include a rectangular cross section approximately equal to the aperture 106 of the housing. In an example, the spacer 196 can include a bellows, which may be adjusted over a range of lengths. For example, such a range can include a range from about 5 cm to about 120 cm. A ruled indicator can indicate the actual distance selected, either in linear units such as inches or centimeters, or in units of diopters (equal to the inverse of the distance in meters, e.g, 4 diopters equals 25 cm). Diopters can be useful units because they are also generally used to indicate a focal length of corrective lenses that may be worn by the patient 108. In an example, the spacer 196 can include an opaque covering to block room light. In another example, the spacer 196 can include a framework and does not need to block light ambient light. In another example, the spacer 196 can be removable to enable spacers of different lengths to be affixed to the housing 102, and to allow the device to be disassembled for storage.

An inner surface of the spacer 196 can be non-reflective, otherwise, it may reflect light to the patient's eyes and cause glare. Examples of non-reflective surfaces include black matte paint or black anodized aluminum. In these examples, the surface can be treated or prepared to reduce or minimize reflectance. In other examples, a non-reflective coating such as black felt can be attached to the inner surface of the spacer 196. In another example, the inner surface of the spacer 196 can be textured to preferentially reflect light back down to the light and away from the patient. In an example, the texture can include triangular shapes, which can include linear triangular grooves. This can be similar to pyramidal texturing used on the surface of solar cells to suppress reflections, although in this example grooves instead of pyramids are adequate since most of the light comes from a single dominant axis, rather than from all directions. However, in another example the non-reflective texture can include pyramids, which generally include a triangular cross-section. Even with the texture, a dark or black surface can also be used, such as obtained with paint or anodizing of aluminum.

The viewing position of the patient 108 is generally located at a fixed position at the end of the spacer 196, furthest from the light. For example it can be a viewport where the patient can place his or her face and look through to see the chart. In an example, the viewport can include a piece that fixes on the spacer 196 and contains two holes, one for each eye. In another example, the viewport can include a single aperture. In an example, the viewport can include opaque covers that block light to one eye, such as enabling measurement with the left eye or right eye alone. In an example, the spacer 196 can include an opaque bellows between the patient 108 and housing 102. A triangular texture of a bellows surface generally suppresses or eliminates reflections and stray light, because incident light is not reflected to the viewport. The bellows can be similar to that used in a camera assembly. In an illustrative example, a bellows can include a rectangular cross-section and can adjust in length over a range of about 5 to about 40 cm. A frame can include aluminum rods can support the bellows structure. The viewport of the spacer 196 can be located in a fixed position, and the housing 102 can be slid forward or backward along the aluminum rods to a desired location. A ruled label or other indicium of distance can be provided in relation to the spacer 196, either on a support or on a base, such as to indicate the distance between the viewport and the chart or to indicator one or more other distances. In an example, the distance can be specified in terms of centimeters or diopters.

Figure 2:
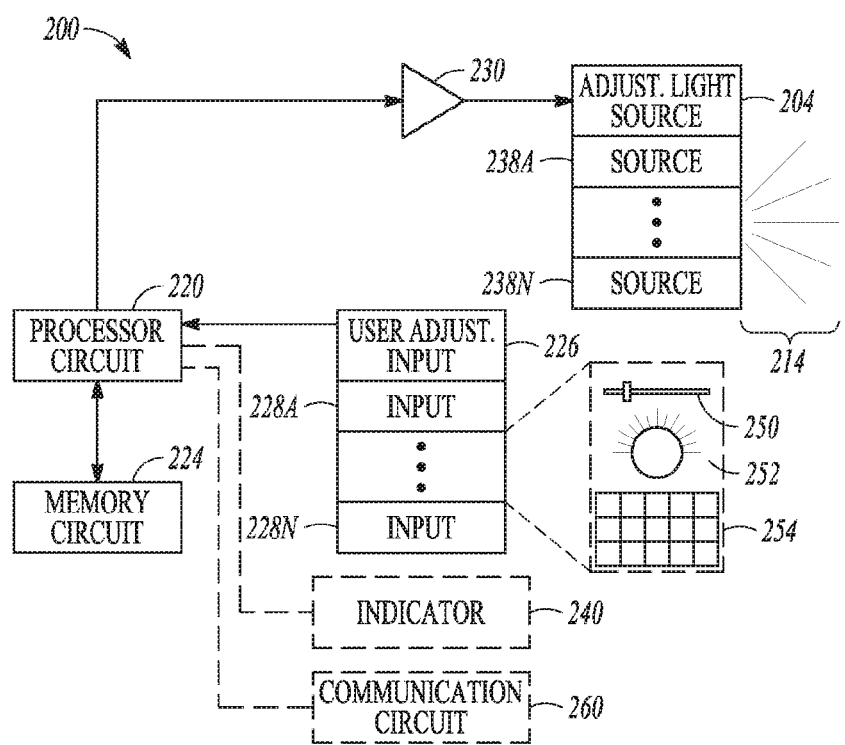
FIG. 2 illustrates generally an example of at least a portion of a system, such as for evaluating visual acuity.

FIG. 2 illustrates generally an example of at least a portion of a system, such as including apparatus 200 for evaluating visual acuity. The elements shown in FIG. 2 can be housed in a self-contained hand-held apparatus, such as shown in the illustrative examples of FIG. 1 and FIGS. 4A through 4D. In an example, portions of a system can be distributed between a hand-held apparatus, and a local assembly such as a tablet, mobile device, or desktop computer, such as shown illustratively in FIG. 3. Other portions of the system can be remote, such as can include a database or other repository of information about one or more lighting products, as illustrated generally in FIG. 3 and as can be accessed such as using the interfaces described in the illustrative examples of FIGS. 5A through 5C (e.g., such as using a tablet, laptop, desktop, or mobile device).

In the example of FIG. 2, the apparatus 200 can include a processor circuit 220 (e.g., an embedded processor circuit or system, such as can include a microcontroller, microprocessor, or other circuitry such as a finite state machine). The processor circuit 220 can be coupled to a memory circuit 224, such as can include instructions that, when performed by the processor circuit 220, cause an adjustable light source 204 including one or more individual sources 238A through 238N to provide illumination 214 having one or more of a calibrated illuminance or a specified color property. The processor circuit 220 can receive information from a user indicative of a calibrated illuminance and a color property, such as using a user adjustable input 226, including one or more individual inputs 228A through 228N. Such inputs can be mechanically-variable, such as can include using a slider 250, a rotary control 252, or a keypad 254. According to various examples, the user-adjustable input 226 can include an analog input, such as a potentiometer, or a digital input such as an optically-coupled encoder or keypad, keyboard or touchscreen. An indicator 240 can be included, such as to provide indicia of a selected illuminance and a selected color property. The indicator 240 can be a passive indicator, such as a calibrated scale aligned with one or more user-adjustable inputs (e.g., as shown illustrative in FIGS. 4A through 4D), or the indicator 240 can be an electronic or digital display, and can even be located remotely as a portion of a separate apparatus and communicatively coupled to the processor circuit 220, such as using a communication circuit 260 (e.g., a wired or wireless networking circuit). In an example, the indicator can provide a reading in a closed-loop manner, such as based on a photocell that directly measures the light output of the LED arrays.

In an illustrative example, the adjustable light source 204 can include LEDs or light sources, such as mention in an illustrative example above, and such having two (or more) color temperatures and two (or more) colors selectable or driven using separate circuits (e.g., using a drive circuit 230). Thus, in an illustrative example, such a configuration of LED arrays can be used to provide any color temperature light from about 2,700° K to about 6,500° K, such as by adjusting the relative output of the two color circuits or by rapidly toggling between the two color circuits using proportions of time specified on each circuit to establish the desired color temperature. For example, pulse width modulation (PWM) can be used to drive one or more LEDs or LED arrays to achieve a desired duty cycle, such as to obtain a desired proportion of output from each of the available color temperature LEDs (or from a selected subset of the available LEDs).

Similarly, hues can be generated by controlling the relative output of LEDs of different colors. For example, mixing light from red and green LEDs provides hues spanning the spectrum from red to green. Mixing red, green and blue LEDs provides hues covering most or all of the CIE color space. Tints may be generated by mixing a colored hue with white light. For example, 50% white and 50% colored light provides 50% tint; 67% white light and 33% colored light provides 67% tint. Such white light can be generated using white LEDs, or using a combination of red, green, and blue LEDs to generate a desired white light proportion. In the example of FIG. 1, the arrays can be arranged to illuminate an object at a "grazing" angle, such as specified to be greater than or equal to about 30° from the vertical (e.g., normal axis from a surface of the object), such as in order to reduce or minimize direct (e.g., specular) reflection off the chart to a patient. Use of two LED arrays, such as symmetrically located, can provide even illumination of the chart.

Use of LEDs for the adjustable light source 204 can provide a wide range of available illuminance, such as at least about 300 lux, or covering a specified adjustable range such as from about 50 to about 5000 lux. According to an illustrative example, the LED arrays can be about 150 cm in a long axis and placed approximately 6 cm laterally offset from a center line. In an example, the LED arrays can be powered using a drive circuit 230, such as including an LM3410 LED driver circuit available from Texas Instruments (Dallas, Tex., United States of America). Pulse width modulation (PWM) can be used to vary the LED intensity. For example, a PWM frequency can be about 1 kiloHertz (kHz), and an illuminance can be adjustable and calibrated over a range of 50 to 5000 Lux. In examples including PWM control, the illuminance can be set by controlling a ratio of on-to-off time in the PWM pulse waveform. For example, if the LED has full power when the signal is high and no power when the signal is low, a 1 kHz pulse that is on for 0.9 milliseconds (msec) and off for 0.1 msec will provide 90% of maximum available intensity.

One or more of a processor or oscillator circuit can be used to generate the PWM signal. In an illustrative example, a person conducting the exam (e.g., a clinician) can set the calibrated illuminance using a potentiometer with a linear or rotary control aligned with a calibrated scale or having a calibrated indicator. In an example, a photodetector can be used to monitor the illuminance and the person conducting the exam can read a monitored illuminance on a display. In yet another example, an illuminance can be set using a desktop computer, laptop, tablet, or mobile device, such as having a user input including a touch screen display, a numeric keypad, or a keyboard, for example.

Other light sources may be used, such as halogen or fluorescent lamps, or discrete LEDs, such as each including an individual lens. For example, the LEDs can each be monochromatic, such as having a color set by the peak wavelength of the LEDs, such as 527 nanometers (nm) (e.g., green) or 570 nm (e.g., yellow). In an example, monochromatic LEDs having different wavelengths can be used in combination in order to provide adjustable hue, such as a selectable hue within as reference to a CIE color space (a CIE1931 color space. for example, corresponding to the examples of photometric observers or colorimetric standards specified in joint International Standards Organization (ISO)/International Commission on Illumination (CIE) documents, such as ISO 23539:2005(E)/CIE S 010/E:2004, entitled "Photometry—The CIE System of Physical Photometry," or ISO 11664-1:2008(E)/CIE S 014-1/E:2006, entitled "Part 1: Standard Colorimetric Observers"). For example, monochromatic LEDs can be driven separately or in groups to enable variation of a color property such as hue or color temperature, across a selectable range.

Figure 3:
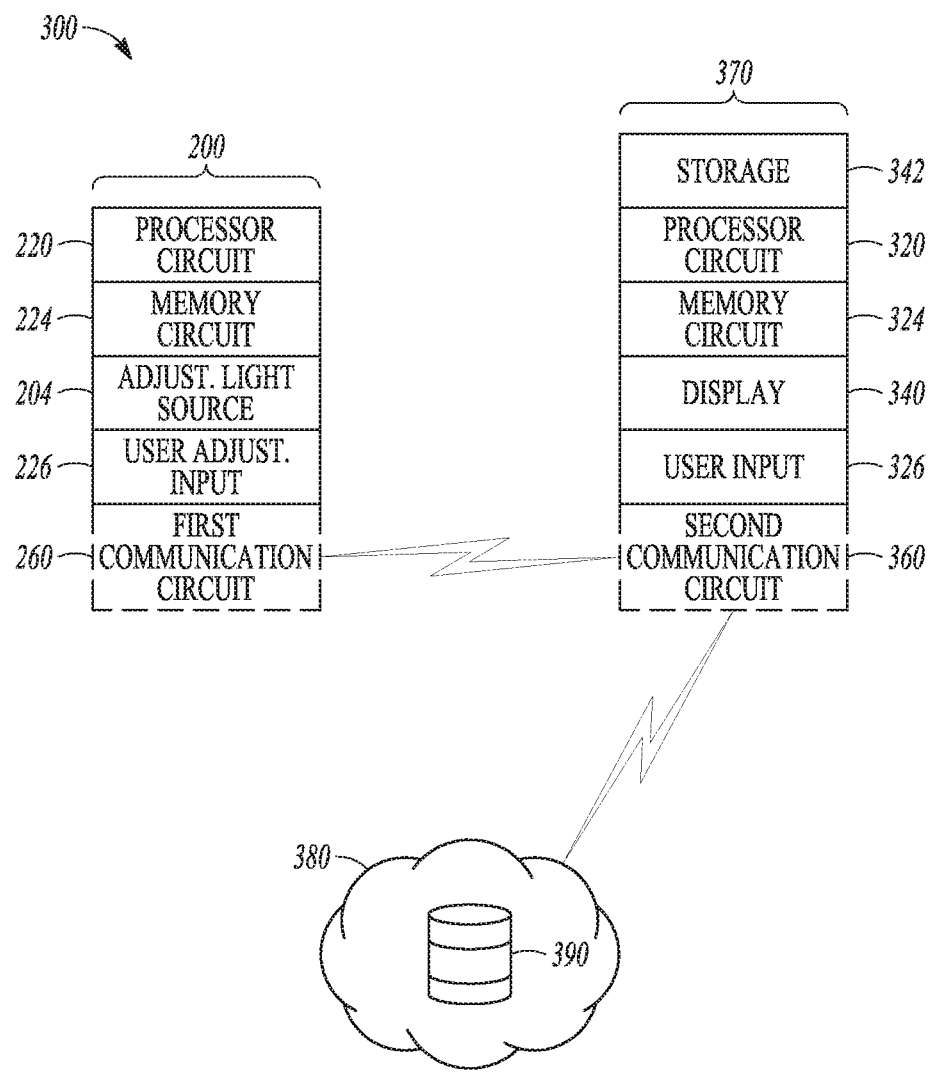
FIG. 3 illustrates generally an example of at least a portion of a system, such as for evaluating visual acuity, or such as for providing a lighting recommendation.

FIG. 3 illustrates generally an example of at least a portion of a system 300, such as for evaluating visual acuity, or such as for providing a lighting recommendation. The system 300 can include an apparatus 200, such as shown and described illustratively in other examples herein, such as FIG. 1, 2, or 4A through 4D. The apparatus 200 can be portable, hand-held, such as including a first processor circuit 220, a memory circuit 224, an adjustable light source 204, a user-adjustable input 226, and, in an example, a first communication circuit 260. The first communication circuit 260 can be communicatively coupled to a second communication circuit 360, such as included as a portion of a second apparatus 370. The second apparatus 370 can include a tablet, a mobile device, a desktop personal computer, or one or more other electronic devices. For example, the second apparatus 370 can include one or more of storage (342), such as a hard disk or non-volatile random access memory (RAM), a second processor circuit 320, a second memory circuit 324 (e.g., a dynamic or static RAM memory circuit), a display 340, and a user input 326 (e.g., a touch-sensitive screen, keypad, mouse, or other control).

One or more of the first apparatus 200 or the second apparatus 370 can be communicatively coupled to the internet 380 or to another network of electronic devices. For example, the internet 380 can provide one or more repositories of data such as a database 390. The database 390 can include information about specific lighting products or other information pertinent to providing a lighting recommendation to a patient. For example, a test of visual acuity versus illumination can be carried out using the first apparatus 200 alone, or under the control of the second apparatus 370, as described in other examples herein. The second apparatus 370 can then provide a lighting recommendation based on results obtained from the evaluation of visual acuity. In an example, the second apparatus 370 can perform a query of information available from the internet 380 including information obtained from the database 390, such as to generate a specific lighting recommendation for the patient, either to be provided directly to the patient or to a caregiver. User interfaces that can be presented to a user are shown illustratively in FIGS. 5A through 5C, such as can be presented using the display 340.

FIGS. 4A through 4D illustrate generally illustrative examples of views of a housing and input configuration for an apparatus 400, such as corresponding to the examples of FIG. 1 or 2, and such as for evaluating visual acuity. The apparatus 400 can include a housing 402, such as shown and described in other examples herein. One or more adjustable light sources (e.g., two arrays of light-emitting diodes in this illustrative example) can be located on or within the housing 402. A viewing aperture 406 can provide access for viewing of an object 410A or 410B under controlled illumination provided by the one or more adjustable light sources. One or more user-adjustable inputs such as a first input 426A or a second input 426B can be used to adjust an illuminance or color property, for example, provided by the one or more adjustable light sources. An indicator, such as a first indicator 440A or a second indicator 440B can provide the user with feedback regarding a selected illuminance or color property. For example, the indicators can be passive (as shown in the examples of FIGS. 4A through 4D), or active, such as can include an electronic display. The object can include one or more of text, an image, an eye chart, or a printed publication such as a newspaper or magazine (or excerpts thereof).

Figure 4A:
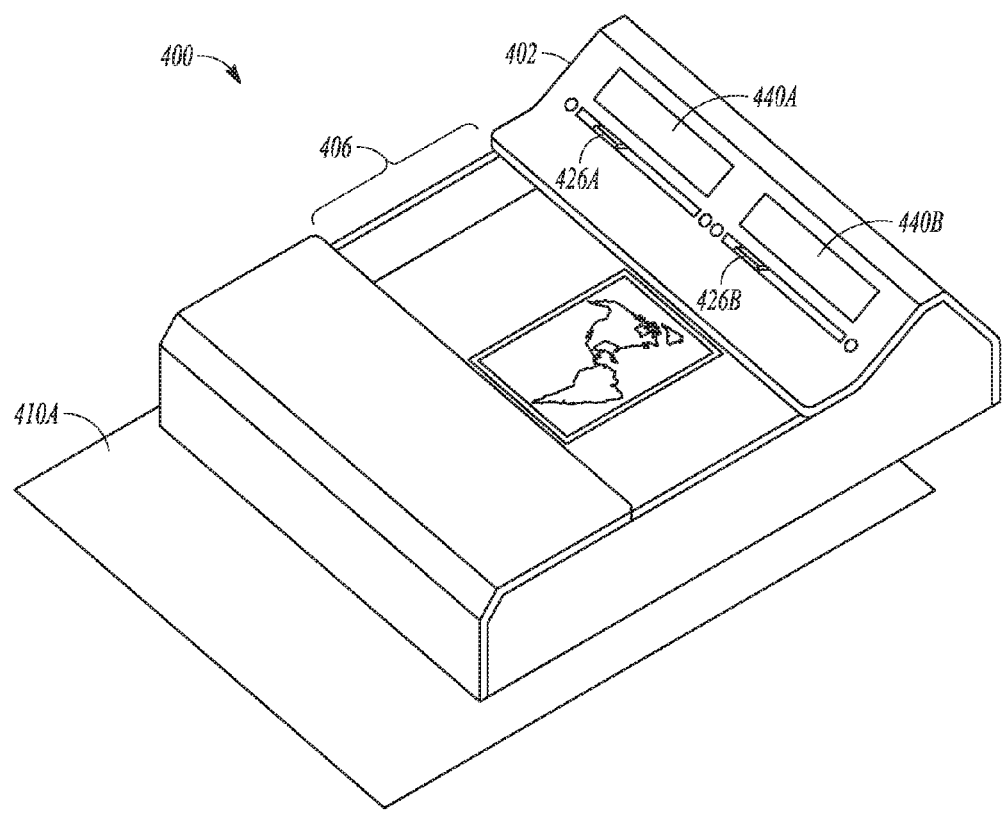
FIGS. 4A through 4D illustrate generally illustrative examples of views of a housing and input configuration for an apparatus, such as corresponding to the examples of FIG. 1 or 2, and such as for evaluating visual acuity.
Figure 4B:
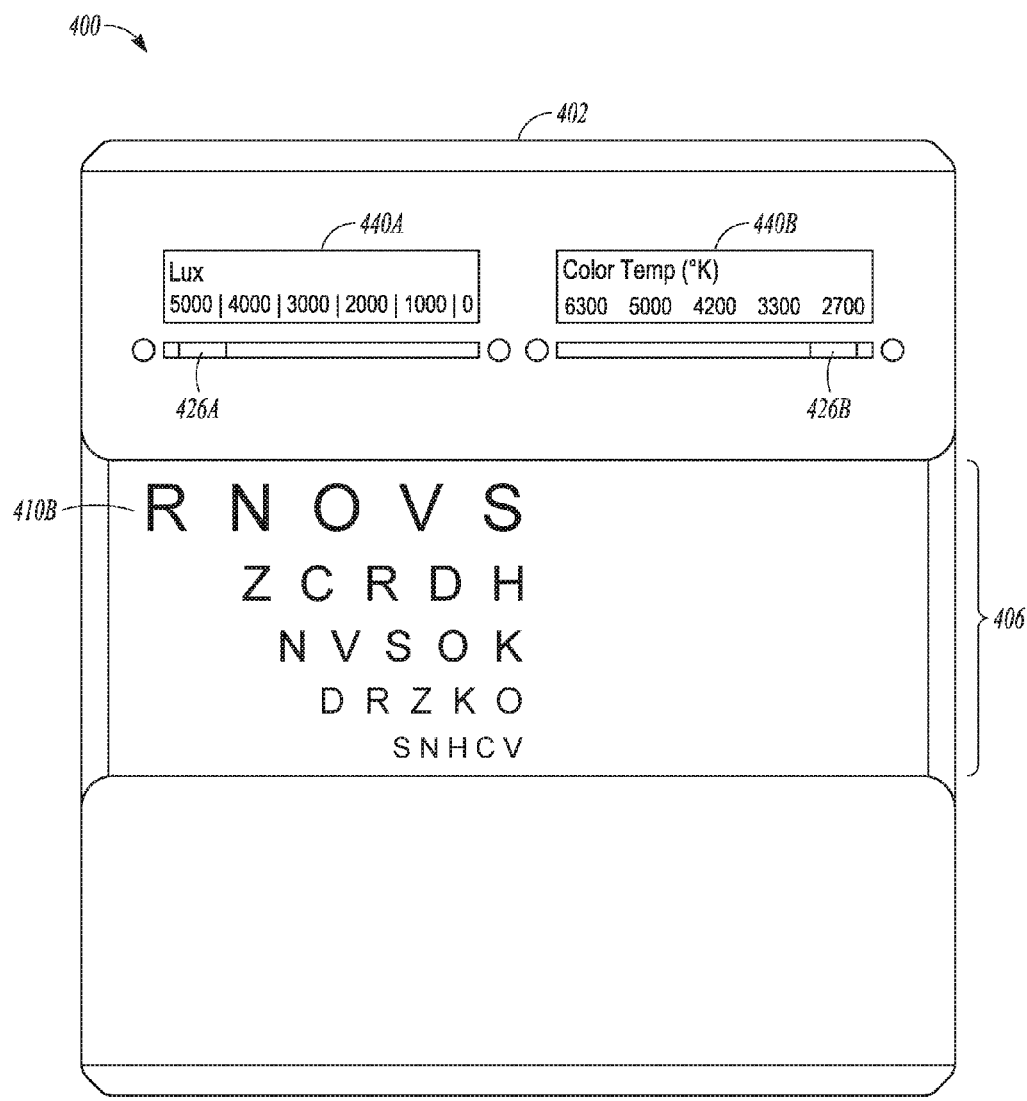
Figure 4C:
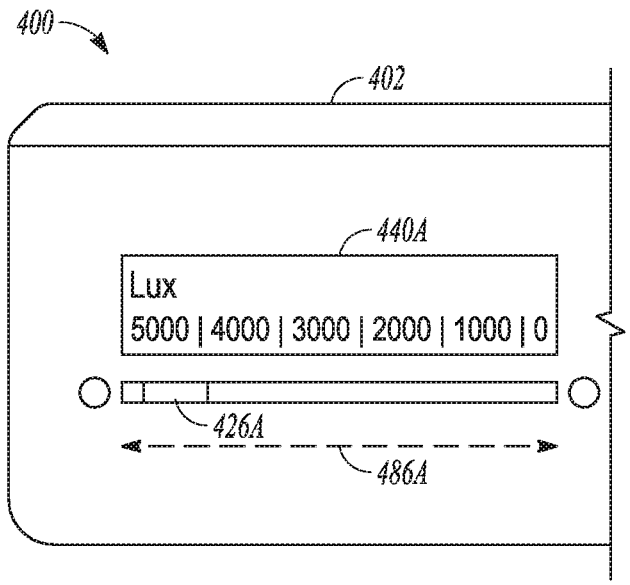
Figure 4D:
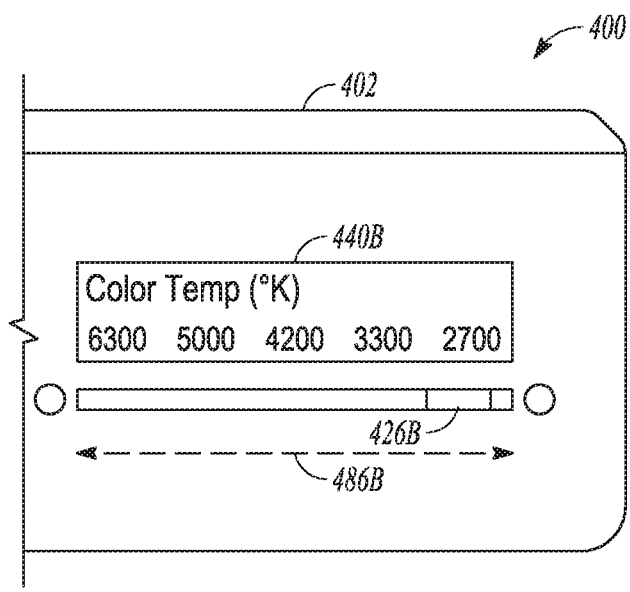

In the illustrative examples of FIGS. 4C and 4D, input 426A or 426B positions can be related to corresponding locations on indicators 440A or 440B, and such indications can be read as the output of the acuity determination. For example, a range 486A of selectable illuminance values can be provided to the user for selection via the first adjustable input 426A (e.g., a first slider). Similarly, a range of selectable color property values 486B (e.g., color temperature in FIG. 4D) can be provided to the user for selection via the second adjustable input 426B (e.g., a second slider). The values shown on the indicators 440A or 440B can be calibrated, such as verified using a photodetector (e.g., in a closed-loop fashion), or through referral or comparison to one or more other standards. In another illustrative example, second adjustment input 426B controls hue, and a property of the hue can be read on indicator 440B, and first adjustment input 426A controls tint, and a property of tint can be read on indicator 440A.

Measurements of visual acuity obtained using the apparatus 400 can be recorded in a variety of ways. In an example, results can be tabulated in terms of lux and color temperature in degrees Kelvin. Other units can be used. For example, results can be tabulated in candelas/square meter and color temperature in degrees Kelvin. In an example, a color temperature need not be varied, and results can be presented exclusively in terms of lux, foot-candles or candelas/square meter. In another example, when the reflectance of the object is known the results can be tabulated in units of luminance, such as candelas per square meter. While various examples refer to illuminance, in another example, the illuminance can be converted or referred to the lumens required to yield a set illuminance at a specified distance, such as, illustratively, lumens at a distance of 1 meter into a cone with an apex angle of 90° that will provide 1500 lux at the surface. Specification of lumens can be convenient because it can assist in generating a lighting recommendation in a form more easily related to commercially-available lighting products or fixtures.

In an example, illuminance specifications for one or more lighting devices or lighting products can be obtained or retrieved, and the illuminance providing best visual function as obtained by the apparatus 400 can be converted to a prescription (e.g., a specific lighting product recommendation) such as including products that are capable of providing the prescribed illuminance level. A lighting recommendation can also include a configuration for the source, such as a lighting angle or distance from a work surface.

As mentioned in other examples described herein, the apparatus 400 can include a processor circuit or embedded processing system, such as an AVR ATTiny860 (Atmel, USA). The embedded processing system can include a communication circuit, such as a Bluetooth communication circuit for communication with a remote device such as a tablet, mobile device, or desktop personal computer. For example, a clinician could use the remote device to one or more of set the illuminance or color property of the apparatus 400, trigger or enable the illumination of the object 410A or 410B by the apparatus 400, record patient responses, graph results, or store the results in a patient record. The apparatus 400 can be used as an element in a system or process to one or more of measure visual acuity under various lighting conditions, prescribe lighting (e.g., providing a lighting recommendation), and even dispense lighting (e.g., by providing a specific lighting product, a specific lighting product recommendation, or enabling purchase of a specific lighting product).

Generally, a lighting product delivers illumination that can be defined such as by the illuminance offered at a certain distance (typically in units of lux or foot-candles). The illuminance can be converted to luminance (typically in units of candelas per square meter), related by the reflectance of the surface, such as the page being read. A lighting product generally also provides certain color properties. For example, for "white" light, a color temperature can be used to characterize the light. For colored light, hue or color can be specified (e.g., red, orange, yellow, green, or blue, as illustrative examples) or wavelength (e.g., 527 or 630 nanometers). In an example, an acuity of a patient with a bright light source is compared to acuity with a less bright source. In this way, the acuity as a function of illuminance and color can be measured. The patient might also report the color and illuminance that provides the greatest comfort. It is then possible to determine one or more of an illuminance or color property at which improved reading acuity is obtained while maintaining a level of comfort that allows the patient to conduct near tasks such as reading. A lighting recommendation or "prescription" can then be used to specify an illuminance or color property, or other parameters. The values of illuminance or color property can be dependent on a contrast of the text being read. For example, greater illuminance might be preferred by the patient to improve acuity when the patient is attempting to read or observe lower contrast media. Accordingly, a lighting recommendation can include providing prescriptions corresponding to different contrast levels, and can be used to establish different recommendations for lighting depending on the contrast. This is important, as people who need greater illumination may also have reduced contrast sensitivity. The apparatus 400 shown illustratively in FIGS. 4A through 4D or described in examples elsewhere herein can be used to rapidly screen through a selectable range of available illumination parameters, such as establishing one or more of a calibrated illuminance or color property.

Figure 5A:
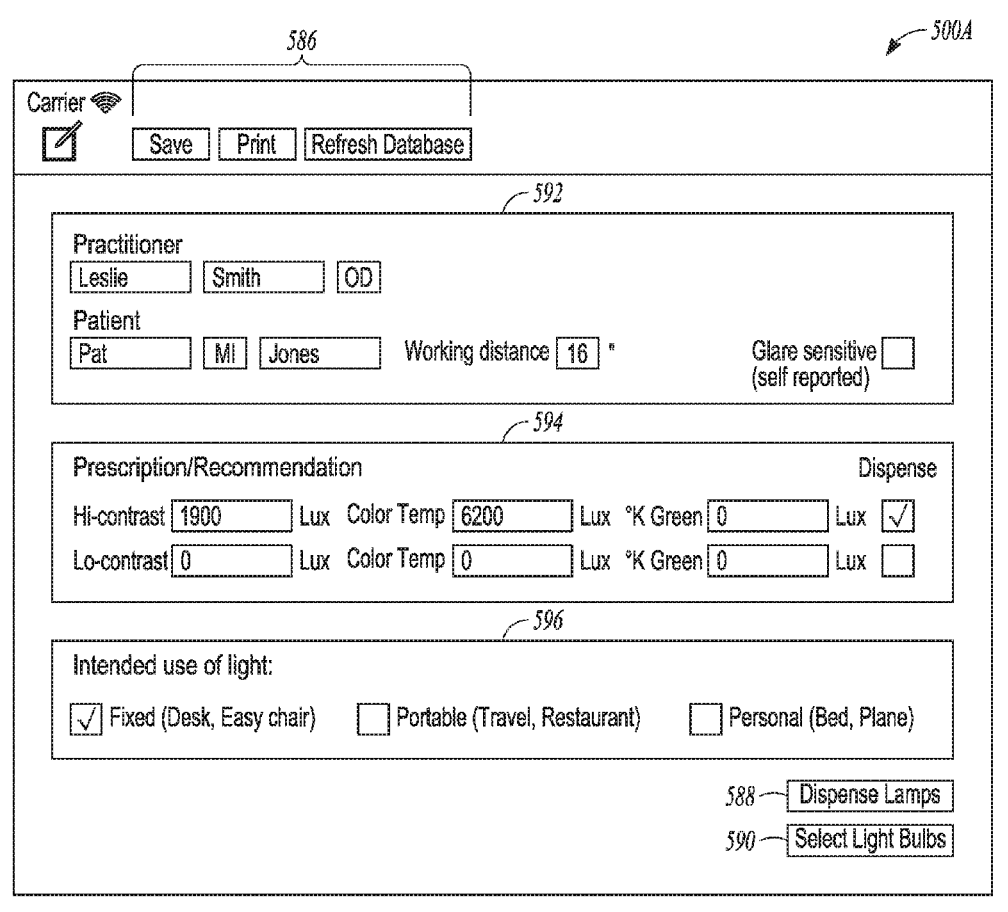
Figure 5B:
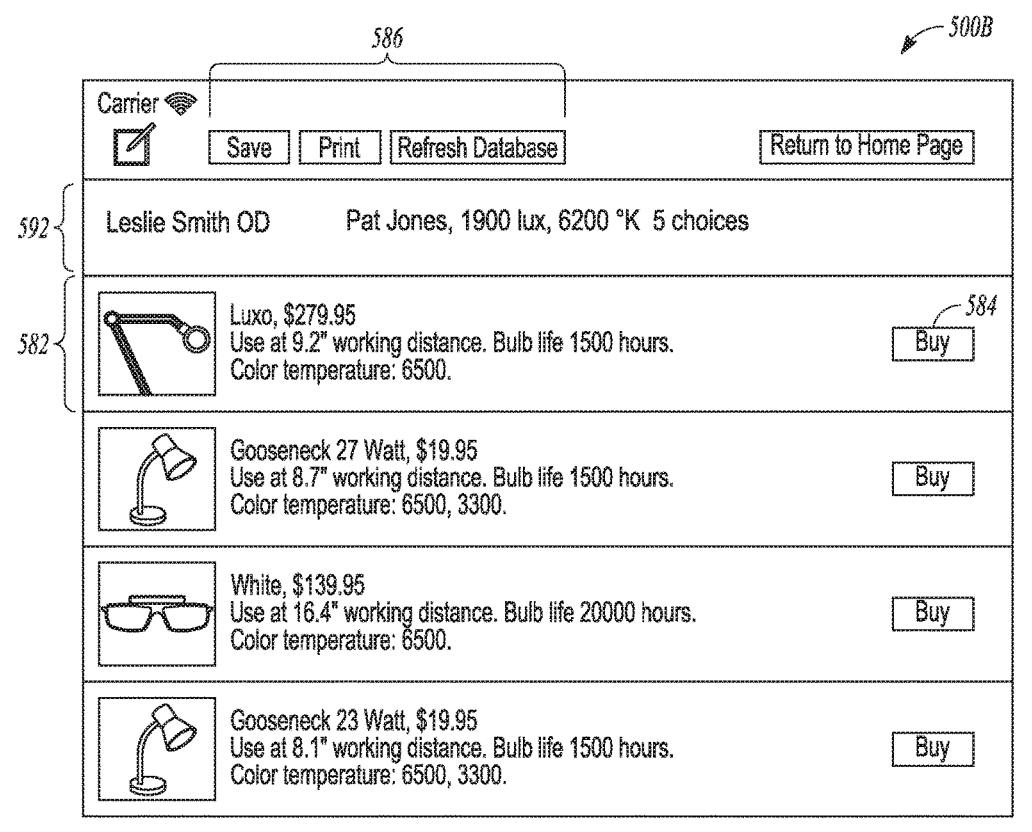
Figure 5C:
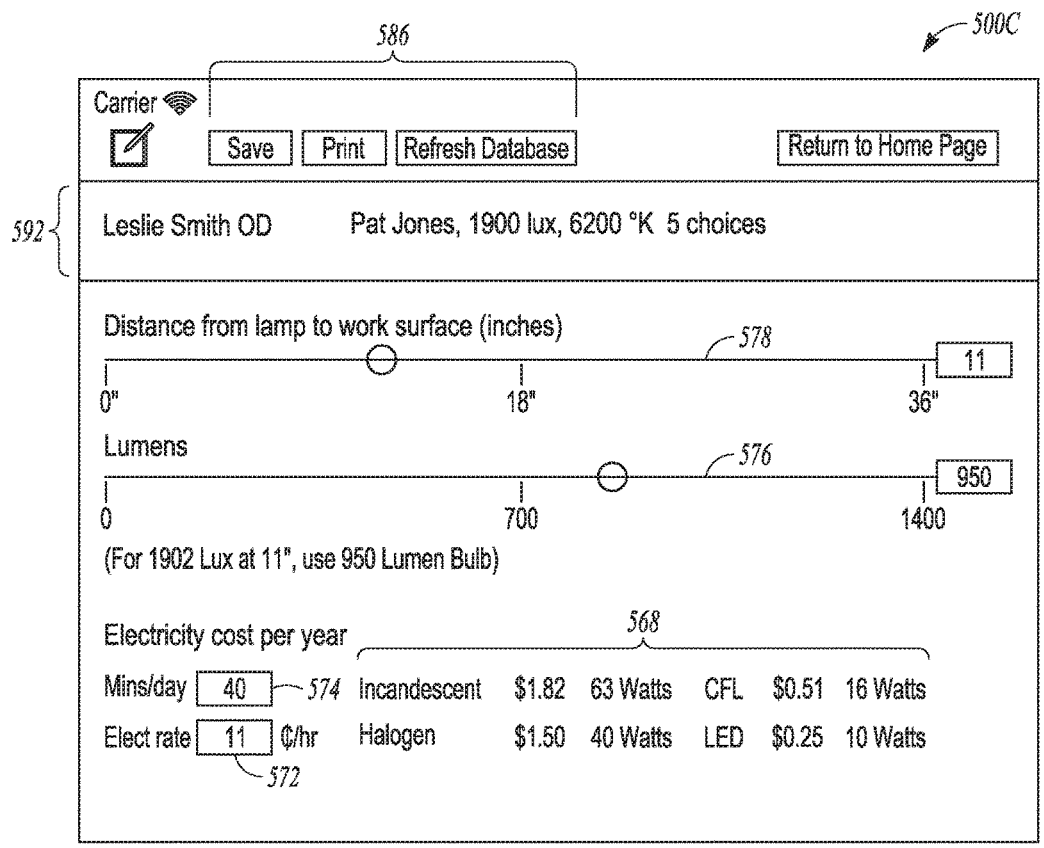

FIGS. 5A through 5C illustrate generally illustrative examples of user interfaces that can be used to one or more of present information to a user such as for providing a lighting recommendation, or receive input from the user. As described in other examples herein, a system can be used to obtain information about lighting helpful for a patient, such as by gauging a response of the patient (e.g., reading acuity) versus one or more of illuminance or a color property of light. Such evaluation can be used to generate a lighting recommendation. Such a recommendation can include one or more of a recommended illuminance (e.g., a value or range of illuminances), a recommended lighting technology (e.g., fluorescent, halogen, LED, incandescent), a recommended distance between a lighting device and a work surface, a recommended color property (e.g., color temperature or hue), a recommended wattage, a recommended lumen output, or a recommended lighting fixture (e.g., desk lamp, floor lamp, task light, or ceiling-mounted fixture).

In an example, the lighting recommendation can include determining, using a database communicatively coupled to the system or included as a portion of the system, a recommendation for a specific lighting product, such as including a position of the specific lighting product with respect to an illuminated surface. The lighting recommendation (e.g., "prescription") can be compared either manually or automatically with an array of available lighting products, which can then be presented to the caregiver or patient. The system can even generate an order or authorization for purchase of a recommended lighting product based on user input. The user interfaces shown in FIGS. 5A through 5C can be presented using a tablet, mobile device, or desktop personal computer, for example, such as running an application or using a web browser or other runtime environment to access such interfaces.

In FIG. 5A, an illustrative example of a user interface 500A can include one or more inputs, such as a menu bar 586 to receive a user input to save, print, or refresh a database of available lighting products. This block can also include a control to trigger generation of an e-mail containing the contents of the page in, for example, Portable Document Format, or trigger generation of a report containing information presented on the page in some other specific format. A profile block 592 can be used to identify one or more of a caregiver, a patient, or selected characteristics of the patient such as glare sensitivity or a desired working distance between the patient and an object being illuminated. The recommendation block 594 can be used to identify one or more of an illuminance (e.g., lux) or a color property (e.g., color temperature or hue, such as green). A user input (e.g., "dispense") can be used to specify that a particular recommendation be generated for a patient, such as causing the system to send a notification to a patient or lighting supplier, or allowing the patient or another user to browse available lighting products corresponding to the recommendation. An intended use of the lighting can be specified such as using the Intended Use block 596. The blocks 592, 594, or 596 can be used to one or more of present information to a user (e.g., a caregiver), or receive information from the user.

Other controls or indicators can be provided, such as a control to "dispense" lamps 588 (e.g., triggering providing a specific lighting product recommendation), or launching a separate menu or application to aid in selecting a lighting product using information about the lighting recommendation from the recommendation block 594 using a control 590.

FIG. 5B illustrates generally a user interface 500B that can include a menu block 586, such as shown in FIG. 5A, and a profile block 592, such as identifying one or more of a caregiver, a patient, or information relating to a lighting recommendation (e.g., a "prescription"). Information included in the lighting recommendation can be used to identify specific lighting products for presentation to a user. For example, a lighting product 582 can be identified, such as having a recommended lighting technology, recommended lighting distance, recommended color property, recommended lumen output, recommended wattage, or recommended lighting fixture style that corresponds to the lighting recommendation. The specific lighting product recommendation can include information about at least one of a lighting manufacturer, a lighting vendor, a product identification, or a price. In an example, a user (e.g., a patient or clinician) can provide a purchase authorization or order, such as using a "buy" button 584 or other input.

In another example, the user or clinician can provide an input to a system including specifying the lighting application or use (such as reading, fine work, cooking, sewing), and one or more other parameters such as whether the patient prefers fixed or portable lighting, whether the fixture is a task light or floor lamp, how much time the patient plans to use the light per day, or what the patient is willing or able to pay. Such constraints can be received by the system, and a database of lighting products can be queried to receive information about products that conform to or are similar to constraints provided by the user, such as to meet patient preferences while also using information about a lighting recommendation in the form of prescribed illuminance or color property. The database can be stored or maintained locally by a caregiver or caregiver network, or the database can include one or more commercial or internet-accessible databases of products. The database need not be restricted to products available for purchase. For example, a database can be used including an array of donated products, or products that can be selected and given to the patient such as subsidized or provided by another entity.

For example, one or more databases of lamp fixtures that provide a range of illuminance and colors can be queried. In an illustrative example, one fixture may provide 1500 lux at a working distance of 12", another may provide 1500 lux at a working distance of 8", and others may provide 1500 lux at working distances of 9" and 14". Further, one product may have a color temperature of 2700° K, another 5200° K, and another 6500° K. The database may provide information about lighting products including task lamps, portable lights, and floor-mounted lights. In this manner, the prescription and user preferences may be used to select fixtures in the database that are more likely to meet patient needs, such as after screening of the patient to identify one or more of a specified illuminance or color property using the apparatus of FIG. 1, 2, or 4A through 4D.

In order to more accurately determine the appropriate lamps to present from the database, each lamp may be measured for its illuminance in lux versus the distance to the work surface. In an illustrative example, one lamp may have a flexible head spanning a distance of 10.5" to 16". At 10.5", the illuminance is measured as 2350 lux, at 12" the illuminance is measured as 1780 lux, at 14" the illuminance is measured as 1350 lux, and at 16" the illuminance is measured as 1000 lux. These values can be fit to a quadratic function to obtain three coefficients, corresponding to the squared term, linear term, and constant term. The database can be queried for all lamps that provide the specified illuminance within their working distance, and the quadratic fit can be used to determine the correct working distance for that lamp. Other fitting techniques, or look-up tables, can be used in addition to or instead of the quadratic technique mentioned above.

In an example, the database can include information based on manufacturer specifications of lighting fixtures, such as a database maintained or provided by a retailer or lighting manufacturer, or using information provided by a retailer or lighting manufacturer. In another example, lighting products can be independently tested, such as to objectively determine one or more of their illuminance or color properties, and the lighting products identified in the database can include products having been tested or qualified according to such measurements, as mentioned above. Generally, the lighting products identified in the database are commercially available, so the patient can purchase them. In an example, a specified lighting product is available from the vision practitioner that provides the lighting recommendation (e.g., "prescription"). In an example, the specified lighting product can be available as identified such as using a user interface similar to interface shown in FIG. 5B, illustratively.

FIG. 5C illustrates generally a user interface 500C that can include a menu block 586, such as shown in FIGS. 5A and 5B, and a profile block 592, such as identifying one or more of a clinician, a patient, or information relating to a lighting recommendation (e.g., a "prescription"). A first sliding control 578 can be used to input a distance from a lighting device to a work surface. A second sliding control 576 can be used to select a lumen output of a bulb, such as having a lumen recommendation determined using illuminance information from the lighting recommendation.

Inputs such as estimated daily use duration 574 for the lighting device and an electrical rate 572 can be received from user, or values can be automatically determined such as using statistical or geographical information. In this manner, the user can identify bulbs from a choice of lighting technologies (e.g., compact fluorescent lamp, LED, halogen, or incandescent bulb) that might best meet the lighting recommendation. Assumptions can be stored and used in order to provide the lighting technique, such as information stored about a cone angle and internal reflectance of a lighting product (e.g., a light fixture), or a bulb shape. An output block 568 can provide an estimate of annual electric cost based on the electric rate 572 (such as a rate determined using information about the user's zip code) and the expected duration of use per day 574. An estimate of the electricity usage of a lighting device can be determined using published or typical efficiency of the source, such as specified terms of lumens per watt dissipated, the usage duration per year, and the cost of electricity. As an illustrative example, a 1000 lumen LED source might have an efficiency of 100 lumens per watt, for a power usage of 10 watts. Assuming 1 hour use per day, or 365 hours per year, the power used is about 3.65 kilowatt-hours (kWhr). At a rate of 10 cents per kWhr, the cost per year can be estimated as 36.5 cents.

In an example, lighting products such as fixtures can be rated for illuminance at a specified distance, such as 16 inches. A lamp illuminance can then scaled by a formula to determine illuminance as a function of distance. For example, each lighting product (e.g., lamp or fixture style) can have an associated scaling formula. In another example, a scaling relation can be used universally across different lightings products. For example, a quadratic dependence on distance can be applied, so that, in an illustrative example, a lamp providing 1000 lux at 16 inches can be assumed to provide 4000 lux at 8 inches and 250 lux at 32 inches, as described in detail according to another example, above.

In one approach, a scaling technique can be used to provide a recommended distance between a recommended lighting product (e.g, a lamp or fixture) and a work surface, based on a lighting recommendation including an illuminance prescription. Other techniques can be used to aid in identifying candidate lighting products. For example, a prescribed color temperature need not correspond to a commercially available value. In such an example, products having nearby values can be presented. In an illustrative example, a range about the prescribed value can be used, such as ±500° K, so that for a prescription of 5200° K, a recommendation can be presented for products having a range of 4700° K to 5900° K.

The interface 500C of FIG. 5C can be useful in cases where a user (e.g., a patient) wishes to change a bulb within an existing fixture to meet a lighting recommendation. For example, the view of FIG. 5C can be used to relate a common commercial rating of a bulb—output in lumens or color temperature—to the prescription. An analytical technique can be used to relate lumen output to illuminance, such as using an approximation to estimate lumen output. In one approach, a lumen estimation technique can include an assumption that the fixture or lighting device emits a cone of light with an apex angle such as 90° or 120°. The light can then be assumed to uniformly illuminate a circle defined by the intersection of the cone of emitted light and the work surface, which has a radius that can be represented by (distance between light and work surface)×tan(apex angle/2), and an area of pi×(radius)².

A fixture or lighting device can be assumed to have a gain given by the fraction of light the fixture reflects back into the cone. The illuminance in lux can be represented by an expression: [(output in lumens)×gain]/(area of circle in square meters). More sophisticated techniques can be used to provide for other source geometries, such as linear sources (e.g., fluorescent tubes), in which case the intersection area with the work surface may be a shape such as an ellipse, rectangular area, parallelogram, or other shape, and such techniques can account for a uniformity distribution at the work surface. The gain and cone angle can include assumed typical values, because lighting fixtures can vary widely. For example, values may be found by matching the results of an analytical model to an illuminance measured for a generally available lamp, such as a common gooseneck desk lamp. In an example, the user can input desired lamp parameters that may be used in the model. In another example, more than one result or recommendation can be provided, such as with each result corresponding to a different set of lamp parameters used for the model.

Figure 6:
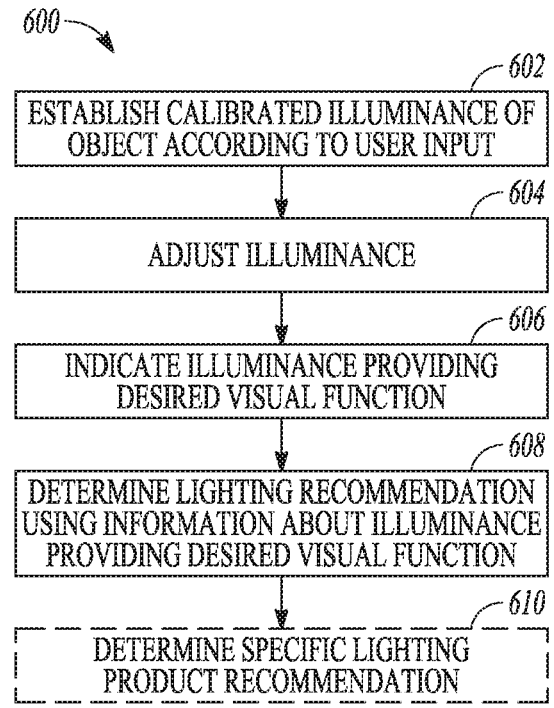
FIG. 6 illustrates generally a technique, such as a method, that can include establishing a calibrated illuminance of an object according to a user input, such as for evaluating visual acuity.

FIG. 6 illustrates generally a technique 600, such as a method, that can include establishing a calibrated illuminance of an object according to a user input, such as for evaluating visual acuity. At 602, a calibrated illuminance can be established, such as illuminating an object. The calibrated illuminance can be established according to user input, as shown and described in other examples herein, such as using apparatus shown above in the examples of FIGS. 1, 2, or FIGS. 4A through 4D, for example. At 604, the calibrated illuminance can be adjusted, such as sweeping manually or automatically through a range of selectable values. Visual function information, such as acuity, can be obtained using a variety of techniques. For example, a user (e.g., examiner, clinician) can set a low level of illuminance and record the smallest characters that the user (e.g., a patient) can read. The illuminance can then be increased and the smallest characters that can be read are again recorded. This can be repeated as many times as the examiner wishes (e.g., for two levels of illuminance, three levels, four levels, or more).

In another approach, the examiner can begin at a low level of illuminance and asks the subject to read the smallest possible line. The illuminance can then progressively increased, and the subject can report each time it is possible to read a progressively smaller line, until the maximum illuminance is reached. In either of these approaches, a person conducting the exam can obtain an objective and quantified recording of visual performance versus illuminance. Many other approaches can be used, such as asking the patient to manually adjust one or more of the illuminance or a color property until the patient achieves a desired level of acuity, either viewing text or another object such as a photograph. At 606, the illuminance provide such desired acuity can be indicated, such as read off the apparatus or provided at a remote device and obtained from the apparatus digitally. At 608, a lighting recommendation can be generating using information about the illuminance providing the desired acuity (e.g., a "prescription"). Optionally, at 610, a specific lighting product or selection of products can be recommended, such as by presenting one or more available lighting products to a user for review.

Tinted Lens Examples

Vision clinicians generally prescribe tinted or neutral density lenses for glasses or contacts. Such tinted or neutral density lenses are in some cases cosmetic, but can provide important functions, such as including one or more of reduced eyestrain, improved perceived contrast, or reduced intensity. Such functions can be important for near or outdoor vision. Many tinted glasses have enhanced transmission in certain wavelength bands, so they appear to have a certain color, such as pink, green, or yellow. Other tinted glasses (such as grey or brown) have neutral density, which can provide generally flat transmission across the visible spectrum. One type of filter can be referred to as a "blue blocker," and can transmit light above a certain wavelength, such as about 510 nm, and has negligible transmission for shorter wavelengths (e.g., 80% transmission at 570 nm, 1% transmission at 450 nm).

It can be time consuming to determine a preferred color for tinted lenses, and in generally-practiced approaches, such determination generally includes fitting and exchanging several trial frames. Such a manual process also generally relies upon a patient's personal recollection as to how one tint candidate looked while then subjectively evaluating another tint candidate. Such recollection and subjective evaluation generally preclude a repeatable comparison between viewing text or a scene with and without a candidate filter, as ambient lighting can be a function of factors beyond the control of the clinician, such as influenced by weather, time of day, time of year, or other factors.

Accordingly, the present inventors have recognized that apparatus and techniques described herein can be used such as to provide a rapid technique for determination of color and tint preferences to aid in selection or prescription of commercially-available lenses that enhance or optimize visual acuity and demonstrate such performance of the lens to the patient. Furthermore, tinted lenses often affect the color or perceived intensity of lighting, and such techniques as described herein can be used to quickly demonstrate the visual effect of the hue or tint characteristics of a particular filter.

Figure 7:
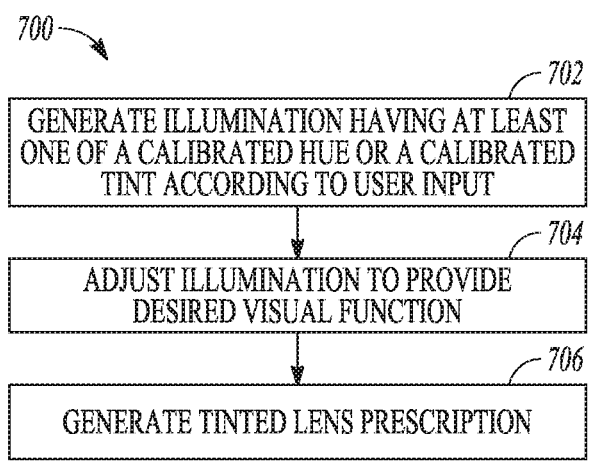
FIG. 7 illustrates generally a technique, such as a method, that can include generating illumination having at least one of a calibrated hue or a calibrated tint according to a user input.

FIG. 7 illustrates generally a technique 700, such as a method, that can include generating illumination having at least one of a calibrated hue or a calibrated tint according to a user input. While the examples described above focus generally on providing a lighting recommendation, such as using information about an illuminance or color property, the apparatus and techniques described herein can also be used for evaluation of illumination to emulate tinted lenses, such as to aiding in prescribing such lenses.

In an illustrative example, the aperture 106 of the apparatus of FIG. 1 can provide a rectangular field of view of dimensions on the order of about 7 cm by about 18 cm wide. Two bars of LEDs can span the long edges of the aperture 106, each with 24 LEDs to illuminate the object 110. The housing 102 of FIG. 1 blocks direct viewing of the LED bars, so the patient sees only the illuminated field of view. In this illustration, each LED bar can include 6 each of white LEDs with color temperatures of 6500° K and 2700° K, 6 red LEDs (625 nm) and 6 green LEDs (527 nm). Adjusting the relative brightness of the red and green LEDs enables varying the perceived color between red and green. Hues corresponding to the colors between red and green can also be generated when these two colors are mixed, following a line connecting the 527 nm and 625 nm points on the edge of a color space. In various operational modes, one or more of the white LEDs and the red and green LEDs can both be enabled. For example, adjusting the relative brightness of the white LEDs enables varying the color temperature in the field of view between about 2700 and 6500° K or a specified tint can be established by mixing output from one or more of the white LEDs with an output from one or more of the colored LEDs.

At 702, illumination can be generated having at least one of a calibrated hue or a calibrated tint according to a user input. For example, a specified tint can be established using white light with colored light added. This simulates the effect of illuminating the field of view with white light and viewing it through tinted lenses. In an example, a white light illuminance and color temperature can be established, as in other examples herein, such as at 2000 lux and 5000° K. Then colored light can be added. Red colored light can be added for example at an illuminance of 500 lux (25%) or 200 lux (10%), such as to simulate pink tinted lenses. Green colored light, for example, can be added at an illuminance of 667 lux (33%), such as to simulate green tinted lenses.

The relative illuminance of the white and colored light establishes the tint, and the hue generally refers to the color of the lenses. In an example, the test apparatus can include a configuration similar to other examples herein (e.g., FIG. 1, 2, or 4A through 4D), but the can include two controls, one for tint and one for hue. These controls may be, for example, slide potentiometers or encoders. The scale on the controls may be read to determine depth of tint and hue. For example, 10% depth of tint can correspond to a colored light illuminance equal to 10% of the white light illuminance (e.g., 200 lux colored and 2000 lux white). In this illustrative example, the hue can correspond to the position in the CIE color space. For example, an orange-yellow hue corresponds to 575 nm, or about 50% red and 50% green.

In an example, the system can be connected to another device that can control the tint and hue, such as providing an indication of the selected or controlled values (e.g., such as having a system topology similar to FIG. 3). In another example, the controlling device can include a table matching the hue and ratio of colored to white light to commercially available lenses, and information can be generated such as hue, a ratio of colored to white light (depth of tint), and a specification for a commercially available tinted lens matching these values, for presentation or transmission to a user.

In another example, a doctor can use one system and a lens supplier can used a second system. In this approach, the doctor can measure a particular value of color and tint specified, for example, as a wavelength in nanometers and tint fraction in percent. The doctor can provide these values to the lens manufacturer, who can then set a second system to these values, such as providing a reference illumination to match the tinted lenses against.

In an example, the test apparatus can include yellow LEDs. For example, monochromatic LEDs such as red, green, orange, or yellow can be used as colored sources. In another example, LED light bars can be used to emit three colors of light: blue; red; and green. In such an example, the relative intensity of the three colors can be controlled to generate a perceived tint, such as using color coordinates near a center of a CIE color space for high percentage tints, or near the edge of the CIE color space for low percentage tints.

At 704, illumination can be adjusted to provide a desired acuity or visual function. For example, a patient can be presented with comparisons of two illuminances and asked to select the most desirable value. The chosen value can then compared to another value. This process is repeated either manually or under automatically-controlled iteration until desired hue or tint values are identified. A range of available hue or tint values can be constrained such as to better match commercially-available tinted lenses.

Information about a patient visual acuity or visual function under various hue or tint values can be used to provide a recommendation, such as a tinted lens prescription at 706. The technique 700 is advantageous because the patient comparison of various hues or tints can be done quickly without changing glasses or filters, the hue or tint can be adjusted to match changing availability or specification of tinted lenses without the cost of obtaining sample lenses or filters.

FIG. 8 illustrates generally a technique 800, such as a method, that can include generating illumination having at least one of a calibrated hue or a calibrated tint according to a user input, including generating illumination having white light for comparison. At 802, an object can be placed under an illumination source. The object can include reading material, a photograph depicting a scene, or other subject matter as in other examples described herein.

At 804, illumination can be generated to illuminate the object, such as having a calibrated hue or a calibrated tint, according to a user input. At 806, illumination having white light can be generated, such as for comparison by a subject with the illumination generated at 802. At 808, if the patient deems one of the available illumination settings as acceptable, then at 810, a prescription for an appropriate filter can be generated. If, at 808, the patient does not deem a present combination of illumination settings acceptable, then the technique 800 can include iteratively cycling back through one or more of 804 and 806 to determine a set of parameters such as one or more of hue, color, or illuminance acceptable to the patient.

In an example, a system can be used at least in part to perform the technique 800, such as to present light to a patient that simulates the effect of looking through a tinted or neutral density lens, by either mixing white and colored light, or generating a hue equivalent to looking through the lens. The light may be variable in properties such as hue, tint and intensity, enabling rapid selection of one or more values that are perceived as acceptable or optimal for the patient. The generated light can illuminate text or a picture of a scene. An input can be provided to allow reconfiguration between white and colored light, such as a switch to toggle between white and color light generation. Such toggling can be used to quickly demonstrate the effect of a simulated filter to a patient. The values indicated as acceptable can be used to generate a specification for a similar commercially-available tinted lens, such as using a chart, lookup table, or other technique to align the received values from testing with an available filter having the desired hue or tint.

As an illustrative example, the aperture 106 of the apparatus of FIG. 1 can provide a rectangular field of view of dimensions on the order of about 7 cm by about 18 cm wide. Two bars of LEDs can span the long edges of the aperture 106, each with 24 LEDs to illuminate the object 110 from about 5 cm above the substrate supporting the object 110. The housing 102 of FIG. 1 blocks direct viewing of the LED bars, so the patient sees only the illuminated field of view.

The object substrate can include text, reading material such as a newspaper page or an eye chart, a picture of an indoor or outdoor scene, or can even be blank to provide solid field. In this illustration, each LED bar can include 6 each of white LEDs with color temperatures of 6500° K and 2700° K, 6 red LEDs (625 nm) and 6 green LEDs (527 nm). Adjusting the relative brightness of the red and green LEDs enables varying the perceived color between red and green. Hues corresponding to the colors between red and green can also be generated when these two colors are mixed, following a line connecting the 527 nm and 625 nm points on the edge of a color space. In another example, the LED bars consist of 6 LEDs with multiple emitters, such as red/green/blue/white.

In operation of a system according to the example above or other examples herein, adjusting the relative brightness of the white LEDs without the colored LEDs enables varying the color temperature in the field of view between about 2700° K and about 6500° K. Adjusting the relative brightness of the colored LEDs enables varying the perceived color between red and green, or over the CIE color space when a blue LED is also present. An unexpected result is that blue blocker filters may be simulated using red and green light sources, because blue light is absent when looking through red or green filters. In an example, white light can also be generated in addition to having adjustable colored light available. Having a capability to generate white light provides various benefits:

For example, both colored and tinted lenses can be simulated if white and colored light sources are available (otherwise, simulating tinted light generally requires overlaying white light with a pure hue). Neutral density filters can be also be simulated in the same system, such as by varying the intensity of the white light with respect to a reference value, as neutral density filters generally reduce the transmission of all wavelengths equally. Also, using an input such as a switch, rapid toggling is possible between a color illumination mode and a white illumination mode. Such toggling quickly shows the patient a difference between viewing an object such as a scene or text with filtered versus white light.

Referring back to FIG. 8, as an illustrative example, at 802, reading material, such as an eye chart or text with or without associated pictures, or a picture of a scene is placed under an illumination source. The scene can simulate specific outdoor conditions, such as snow covered hills, a lake, a forest, a yard, a sports scene such as a golf course, a baseball or soccer field, weather conditions such as a clear or cloudy day, and colors representative of various times of day. Thus, it is possible to provide a controlled, repeatable representation of actual conditions that the patient might encounter without leaving the examination room, such as when the depicted conditions are not actually occurring outside.

At 804, the color of the light can be varied to find a value that is most pleasing to the patient. At 806, the white light can be generated (such as by switching a system from a color light generation mode to a white light generation mode), such as to demonstrate the difference between viewing with and without a simulated filter.

At 808, if the patient is satisfied, the test can be declared complete. If not, the light is switched back to colored and varied to a new set of one or more values of hue, tint, or illuminance at 804. The patient can then be shown the comparison to white 806, and the process can be repeated until the patient is satisfied. If an acceptable set of values are indicated at 808, then a filter prescription can be generated at 810, such as for a specific filter corresponding to desired values related to color identified at 804.

In an example, the white light for comparison can include a color temperature of approximately 6,000° K to simulate sunlight. In another example, the color temperature of the white light can be about 3,000° K to simulate warm white indoor lighting. In another example, the color temperature of the white light can include one or more other values. In an example, the colored light comprises a mix of white light and a hue to simulate a tinted filter. For example, the color can be established first, and then white light can be added, such as according to a percentage scale. For example, 10% white can represents a 10% tint. 50% white can represent represents 50% tint.

In another example, white light of reduced intensity can be presented according to a percentage scale to simulate one or more neutral density filters. In such an example, 10% can represent a 10% transmission filter (e.g., reference value is 5,000 lux and 10% value is 500 lux). The system can be toggled to present white light set to the reference value (e.g. 5,000 lux) so the patient sees a comparison of the intensity with and without a simulated neutral density filter. In an example, the system has a switch that toggles between only presenting white light and presenting colored or colored plus white light. In an example, the white light used for comparison has a preset color temperature such as 6,000° K to simulate sunlight or 3,000° K to represent warm white indoor light. In another example, the white light color temperature is adjustable. In another example, the system is connected to a control circuit (such as a computer, tablet, mobile device, or embedded system), such as can control a depth of tint and the hue, and provide an output indicating values. In another example, the control circuit includes a memory or is coupled to a network having information relating a hue and ratio of colored to white light to commercially-available lenses, and the readout may include information such as the hue, the ratio of colored to white light (depth of tint), and a specification for a commercially available tinted lens matching these values.

In another example, the system can include LEDs configured to generate a specific monochromatic color. In such an example, monochromatic LEDs such as red, green, or orange, yellow can be used as colored sources, and hues are not generated. One or more of a measured intensity or color of the tint can be used to generate a prescription for a commercially-available lens.

In an example, the system can include or can be communicatively coupled to a general-purpose or embedded processing system such as a computer, tablet, smart-phone, or other device, such using one or more of a wired interface such as a Universal Serial Bus (USB), or through a wireless interface such as Bluetooth. The processing system can be coupled to a memory storing instructions that when executed by the processing system control one or more of the hue or depth of tint of the illuminance.

In an example, a patient can be presented with a comparison of two depths of tint and asked to select the most desirable value. Information indicative of a chosen value can be received and compared to another value. This process can be repeated until an optimum value is found. In an illustrative example, each depth corresponds to how the field of view would be perceived if it were illuminated with white light and viewed through a specific commercially-available tinted lens. Such a procedure can be performed in a manner similar to determining refraction using trial lenses, where illumination alternatives are presented and a subject provides an indication of which of the presented alternatives is preferable. In this example the patient is asked to compare paired values of tint, as an illustrative example. In other examples, the patient can be presented with three or more values. Use of apparatus and techniques as described herein allows such comparison to be done very quickly, without requiring physically changing (e.g., swapping) glasses or filters, and the color of the light can be set to match any available tint without the cost of obtaining sample lenses or filters because such lenses or filters can be simulated.

In another example, an illuminance of the white component of tinted light can be varied until a desirable depth of tint is found. Information obtained from a network, a lookup table, or a chart can be used to match a desired illuminance to one or more commercially-available tinted lenses. In some cases, a filter has the effect of changing color temperature. For example, a 400 nm blue blocker filter generally includes such a short cutoff wavelength that it appears clear, removing only a small fraction of blue light. The visual effect is to, for example, make 6000° K light appear to have a color temperature of approximately 5000° K. In this illustrative example, a patient may be presented with white light of two color temperatures, with the switch toggling between a reference color temperature of approximately 6000° K—corresponding to sunlight—and 5000° K, corresponding to viewing sunlight through the 400 nm blue blocker filter. In this manner, short wavelength blue blockers can be simulated.

FIG. 9 illustrates generally a technique 900, such as a method, that can include placing an object depicting a scene under an illumination source, including generating illumination having a calibrated illuminance. Mobility—the act of moving from place to place—can be difficult and dangerous for people with low vision. Objects with low visual contrast, such as a curb or step, are often difficult to see, turning them into real hazards. Lighting conditions, such as shadows, may further deteriorate an ability to identify hazards. Many with low vision wear glasses or fit-overs having colored lenses, such as to improve contrast acuity.

For example, blue blocking lenses pass light longer than a cutoff wavelength, and block shorter wavelength light. The blue sky can be a source of glare, so wearing blue blockers can reduce glare on bright sunny days and can increase perceived contrast. Similar effects can be found with other color lenses in other lighting conditions. Neutral density (ND) lenses, which generally attenuate all wavelengths equally, can also reduce glare and can increase perceived contrast. ND lenses are available in grey, or with a green or brown tint.

Other lenses are available in a variety of colors—typically green, yellow, orange, amber, red, plum and blue, and a variety of tints ranging from <4% to >70%. Tint generally refers to the proportion of white transmission; for example, a 20% tint lens transmits 20% of white. An effectiveness of colored lenses generally depends on lighting conditions. One lens may work well on a bright day, such as a blue blocker or strong neutral density lens, and may have no benefit or may even increase hazards at dusk on a cloudy day or indoors. For these reasons, lens color and tint are generally assessed under a variety of conditions, which may vary depending on location, time of day, time of year, and the weather.

Eye care professionals (ECPs) generally prescribe colored lenses for patients. The ECP may see a patient once a year or less, for a visit typically lasting 10 to 30 minutes. Filter evaluation generally employs trial frames, which are glass frames fitted with various filters. The ECP might take the patient outside and have them try filters to find one they prefer. This procedure is time consuming, and often not practical in the limited time available for an appointment. It requires the patient remember how a scene looked with one filter in order to compare to another. The procedure is purely qualitative, and has no quantitative measure of performance.

The present inventors have recognized that it is therefore extremely unlikely for the ECP to evaluate colored lenses under the range of lighting conditions that the patient will face while wearing the lenses, and virtually impossible to evaluate the wide range of available filter colors and tints available. For this reason, it is desirable to have a system that enables the ECP to present potential hazards to the patient as they would be seen through tinted lenses under various lighting conditions, to be able to sweep through a wide range of filter options to rapidly home in on a preferred color and tint, and to provide a quantitative measure of performance.

Color pictures of indoor or outdoor scenes can be presented to a patient while illuminated with light that simulates the color and tint of available lenses. The light can be formed as hues by mixing colors such as red and green, with white added to simulate tint. The light intensity can be preset to simulate a certain lighting condition. The scenes being illuminated can contain features, such as renderings having a green or brown tint to assist in simulating tinted neutral density filters, and may have additional color modifications to improve simulation.

A technique according to example can include presenting a picture of a scene to a patient illuminated with colored light. Color and tint can be varied to find the preferred values as indicated by the patient. The pictures of scenes can also include features to quantitatively evaluate visual or contrast acuity. The selected values of color and tint can be received and used for determination of a recommendations for color filters.

Apparatus and techniques as described herein can also be used to rapidly assess a patient preference to establish a filter that can improve visibility of hazards or objects, where the filter is selected from among a wide range of choices, thereby improving safety. Apparatus and techniques as described elsewhere herein (such as in relation to FIG. 1, 2, or 4A through 4D) can be used to perform the technique described herein in relation to FIG. 9.

For example, a picture of a scene can contain an image of one or more objects such as provided a calibrated rendering of the one or more objects. One or more light sources can be used to uniformly illuminate a viewed portion of the image, and a viewing aperture can be used to block direct view of the light sources. A processor circuit can be used to control illumination, such as vary one or more of an illuminance, a color, or a tint of the light sources. Optionally, an overlay can be placed between the viewer and the scene, either over the aperture or directly on the scene. This overlay can be grey to provide shading, or colored to provide colored tinting to the scene.

In an illustrative example, the object being illuminated can be a picture of an indoor or outdoor scene. The outdoor scene may show any common place, such as a yard, a flower garden, a house, a street, a sidewalk, a forest, a sports scene such as a golf course, etc., or an indoor scene, such as a hallway, stairway, room, entry way, kitchen, office, garage. The outdoor scenes may be representative of different conditions that would present different lighting, such as a sunny day, a cloudy day, summer, winter, morning, mid-day, dusk, and the indoor scenes may represent different types of indoor lighting. Such examples are illustrative.

Many of the scenes mentioned above may not be observable at the time of assessment. For example, an assessment in an ECP's clinic would require taking the patient outdoors, which may not be practical. An assessment on a cloudy day precludes evaluating conditions on a sunny day. Many indoor conditions, such as a dark hallway or kitchen may not be observable in a clinical setting. The pictures include a calibrated rendering of one or more objects, referring to objects that are calibrated in one or more aspects.

In an example, the calibrated rendering includes images of hazards, and the calibration relates to properties such as one or more of location, size, and contrast, and color. In another example, the objects include calibrated features of varying size to allow measurement of the patient's visual acuity, or different contrast to allow measurement of the patient's contrast acuity in the context of looking at a scene (as compared to, for example, a letter chart). Contrast may be graded over a distance in order to measure contrast acuity as a function of spatial frequency. Such a scene can be considered a new form of eye chart.

Generally-available charts are printed with black letters on a white background. By contrast, a chart for use with the techniques as described herein can be used measure acuity in a more realistic context. In an example, the pictures are rendered using a true color representation of the scene. In another example, the picture colors are adjusted so colored illumination provides an accurate representation of how the scene would appear through a color filter being simulated, because illuminating a scene with colored light may not precisely simulate how the scene looks through a filter.

A transmission function for certain filters can be complicated, and without being bound by theory, may not be easily simulated with a limited number of monochromatic sources. For example, color may be swept by simply combining red and green light to provide all the hues between red and green.

However, use of an overlay can still provide a constrained and easy-to-use evaluation scheme, such as limiting a user selection to a simple ratio of red to green while still providing simulation of a more complex filter transmission. Another example can include adding or using blue light, such as to simulate filters with blue or purple content. Such a scheme can be used to approximate how most scenes look under various color filters without tint. White light may be added to simulate tint, and adjusting the color mix in the scene may provide further color correction. For example, if a scene viewed through a simulated filter has subdued reds, the red colors in the pictures may be corrected in the picture rendering to appear subdued to aid simulation.

The availability of white light adds the benefit of providing a direct comparison between how the scene might appear through a filter and how it might appear without a filter, such as by allowing switching between colored and white light representations (as mentioned above in relation to FIG. 8). White light can be added with constant illuminance as the tint is varied. This can be accomplished in an example by establishing a fixed illuminance that can be represented by $L=W+LH$, where W can represent the white illuminance and LH can represent the illuminance due to the tint, with $LH=R+G$, where R and G can represent the illuminances due to red and green sources in a two color system (a similar extension is possible for a three color system with blue added). As $W=T*(R+G)$, where T can represent the tint fraction, $L=(R+G)*(1+T)$.

Using these equations, it is possible to control a value giving the tint and a value giving the ratio of R to G to properly set the intensity of the R, G and W sources. In an illustrative example, light emitting diodes (LEDs) can be used light sources, such as red and green LEDs (e.g., Cree MLERED-A1-R30-H2-0-00003 and MLEGRN-A1-G20-K3-0-00003) as the color sources and white LEDs (e.g., Cree MLCAWT-A1-1A0-N2-0-00003) as the white sources. The LEDs are driven using electronics, for example, with intensity controlled using pulse width modulation. A wide range of illuminance can be provided, such as to simulate the extremes of lighting in a home environment—on the order of 50 lux to about 100 lux, and outdoor light, which may exceed 10,000 lux. To provide such a large dynamic range, in one example, multiple ranges of LED drive current can be used, such as having current pulse width modulated to provide calibrated illuminance adjustment.

The currents can be set using multiple sense resistors and a driver IC such LM3410 LED driver circuit available from Texas Instruments (Dallas, Tex., United States of America). In this manner, a number of tinted filters can be simulated. Such filters can include blue blockers, which are generally long-wavelength pass filters with a sharp cutoff; for example, a 527 filter has a cutoff at 527 nm: and generally wavelengths shorter than the cutoff are blocked, and all wavelengths longer than the cutoff are passed.

Other filters include neutral density filters, which generally attenuate all wavelengths equally. Neutral density filters are generally available in three shades: grey, green and brown. The green and brown filters generally add a slight green or brown tint to the scene. Yet another class of filters are tinted filters, which are generally available in a range of colors, including green, yellow, orange, amber, red, plum and blue, and a range of tints, from approximately 4% to 70%. Tint generally represents a fraction of white light transmitted.

Each of the classes of filters mentioned above can be simulated using apparatus and techniques described in the examples herein and elsewhere in this document. For example, combining red and green light in different ratios can be used to simulate blue blockers, such as approximating a color mix seen through a filter. Fine adjustment of a color balance in a scene, such as through adjusting the color rendering of the scene when printed, can further improve the match.

Using white light and varying the intensity can be used to simulate an effect of one or more neutral density filters. Some neutral density filters have a green or brown tint. Adding a uniform green or brown overlay on the system, either above the viewing aperture or on the picture, or enhancing the pictures with a green or brown tint can be used to simulate the effect of green or brown filters. Using a mix of red, green and white light provides a capability to simulate most tinted filters.

A high-color-temperature white, such as 6500° K, has about 30% blue content. This can provide a blue component to simulate common colors such as highly tinted plum. Some filters are shaded rather than tinted, shading being the effect of adding black as opposed to white. Adding a gray overlay on the system can be used to simulate shaded tones. Shading and tinting can be combined, as these compensate for each other. For example, 20% shading and 20% tinting a neutral tone results in the same neutral tone. Thus, a grey overlay, such as a gray plastic filter, can be placed over the viewing aperture to provide a shaded tone, and then white light can be added to sweep the tone from shaded through tinted.

The system can include or can be coupled to a processor circuit and a memory, such as storing instructions that when performed by the processor circuit cause the circuit to receive information indicative of one or more of a preferred color or tint, and to generate closely matching selections for one or more commercially-available tinted filters.

For example, a user can provide color and tint information, and part numbers or vendor information for closely matching lenses can be provided. A number of calibration techniques are possible. In one approach, two digital pictures of a scene are taken, one through a filter and one with colored lighting. Comparison of these pictures indicates the lighting best matching the view through the filter. This process may also be carried out manually, for example, by illuminating two adjacent pictures, one with white light and viewed through a filter and the other with colored light.

In FIG. 9, the technique 900 can include at 902, placing an object (such as a scene) under an illumination source. The scene can represent or depict a location with potential mobility hazards. The scene can have objects of calibrated size or calibrated contrast, such as to enable quantification of the effect of the filter.

At 904, illumination can be generated having a calibrated illuminance, such as to simulate a light level typically found in the scene. For example, a scene of a hallway might be set at about 100 lux. An outdoor scene on a cloudy day might be set at about 1000 lux, and a scene on a sunny day might be set at about 20,000 lux. Depending on the type of filter being simulated, at 906, adjustments can be made to one or more of color, tint, and illuminance, such as to find a value best suited to the patient based on the preference of the patient.

For example, for neutral density filters, the intensity can be reduced to a preferred value. For blue blockers or color filters, the color can be adjusted. For tinted filters, the color and then the tint can be adjusted. After adjustment, at 908, a determination as to whether the filter is acceptable can be made.

Such a determination can be made according patient preference, or by the ability to distinguish objects in the picture with finer detail or better contrast, as illustrative examples. At 910, once candidate filter parameters are found, a prescription can be generated. At 912, the prescription, such as including one or more of density, color, tint, can be used to select the nearest available filter or a subset of candidate filters most closely matching the prescription.

Examples Including Evaluating a Presence or Degree of Traumatic Brain Injury (TBI) or Mitigating TBI-Induced Discomfort Using Information about Color Preference or Illuminance Traumatic brain injury (TBI) is a brain disorder characterized by a number of symptoms, such as including light sensitivity. Forms of TBI include: injury from, for example, blast or auto accidents, which has sudden onset and long duration; concussion, which has sudden onset and short duration; and Chronic Traumatic Encephalopathy (CTE), which manifests as a progressively debilitating condition.

Generally, assessment of TBI is performed qualitatively. No quantitative measurement is generally available, making progression difficult or impossible to gauge. The progression can be recovery, as with concussion, or as with CTE, a steady worsening. The present inventors have also recognized, among other things, that a need exists to mitigate the effect of the symptoms of TBI.

In one approach, light sensitivity can be evaluated in terms of one or more of color preference or illuminance preference corresponding to a specific color, such as using apparatus and techniques as described elsewhere herein (such as in relation to FIG. 1, 2, or 4A through 4D). Without TBI, a patient may generally indicate a color preference based on visual acuity gain. With TBI, a patient may additionally express a preference based on a hue that minimizes discomfort. Such preferences can be quantified, and can be evaluated to determine changes over time. For example, a baseline can be established, and a degree of deviation from the baseline can be used to quantitatively diagnose a presence or progression of TBI.

The present inventors have recognized, among other things, an unexpected result that light sensitivity, as experienced with TBI and related conditions, will change color preference when color preference is systematically evaluated such as using apparatus or techniques as shown and described herein (e.g., using a calibrated source of illumination to illuminate an object such as a chart, a plain surface, or photograph of a scene). For example, a person unaffected by TBI will prefer a hue (e.g., a mix of colors) that provides the best acuity and clearest vision. As an illustrative example, a person unaffected by TBI may prefer a mix of 60% green and 40% red, forming a yellow hue (e.g., a "baseline" determination). If the same person is experiencing TBI, such as a concussion, a desire to see a more soothing color will also affect color preference. As an illustrative example, the person experiencing TBI may now prefer a hue that is a mix of 85% green and 15% red. The change between non-TBI and TBI preference is quantifiable, such as providing a measurement indicative of the presence or degree of TBI. A color-based approach for quantifying TBI can provide an improvement over a purely intensity-based assessment. For example, if a football player wants to be cleared of a concussion (e.g., to "spoof" the test in order to retain eligibility to play), the player may report tolerance to a higher illuminance. However, such a player would find it more difficult to somehow memorize a baseline hue.

Illuminance information (or other indicia of brightness) can provide an additional indication of severity of TBI, because the light sensitivity associated with TBI will generally make the desire to choose a soothing color stronger. In an example, such as using the apparatus and techniques described herein, an illuminance and a hue can both be varied. For example, the hue can be set to value indicated as preferred by the patient, and then the illuminance at the selected hue can also be set to a value indicated as preferred by the patient. In another example, an illuminance can be set at a higher level as compared to a level corresponding to a patient tolerance for white light, and the hue can then be set to a value indicated as preferred by the patient. For example, if the patient indicates a tolerance of a level of 500 lux of white light, the hue selection can be performed using an illuminance level of 1000 lux.

A measurement of one or more of hue or illuminance preference can be be made when a patient is normal or otherwise asymptomatic. As an illustrative example, a baseline set of values of one or more of hue or illuminance preference can be obtained when a football player does not have a concussion. As another illustrative example, a measurement can be made on a person who may be at risk of CTE, but does not yet show symptoms. Subsequent measurements of hue or hue and illuminance can then be used to indicate changes. As illustrative examples, a normal person may prefer illuminance values ranging from about 2000 to about 4000 lux, and a person with TBI may prefer considerably less, in some cases 200 lux.

Apparatus for performing the measurements described above related to TBI can include apparatus as shown in one or more of FIG. 1, 2, or 4A through 4D. Other apparatus can be used. For example, a light source used for testing can include a flat panel display, such as connected or comprising a personal computer, a laptop computer, a tablet device, or a handheld device, as illustrative examples. Such devices can provide a low-cost testing platform having programmability. In another example, the light source can include one or more light emitting diodes (LEDs), such as to provide greater illuminance than is provided by generally-available flat-panel display devices such as liquid crystal display (LCD) devices. As described in other examples herein, selection of one or more of hue or illuminance can be used to semi-automatically or automatically recommend or prescribe lighting that provides the best combination of comfort and illuminance, so that the patient can best carry out normal tasks such as reading or fine work.

Various Notes & Examples

Example 1 can include or use subject matter (such as an apparatus, a method, a means for performing acts, or a device readable medium including instructions that, when performed by the device, can cause the device to perform acts), such as can include or use a system to evaluate illumination for a patient, comprising a housing, an adjustable light source mechanically coupled to the housing and configured to illuminate an object for viewing by the patient on an axis substantially perpendicular to a surface of the object, a user-adjustable input coupled to the adjustable light source, the user-adjustable input configured to obtain information from a user indicative of a calibrated illuminance and a color property to be provided by the adjustable light source including providing a range of adjustable illuminance and color properties selectable by the user, and an indicator configured to provide indicia of a selected illuminance and a selected color property to the user. In Example 1, the adjustable light source is configured to provide light having an illuminance in excess of 300 lux, the housing is configured to provide a first specified distance between the adjustable light source and the object for viewing, and to obstruct viewing of the light source directly by the patient, and the calibrated illuminance is established at least in part using the specified distance provided by the housing.

Example 2 can include, or can optionally be combined with the subject matter of Example 1, to optionally include a calibrated illuminance and color property that are independently adjustable.

Example 3 can include, or can optionally be combined with the subject matter of one or any combination of Examples 1 or 2 to optionally include a housing comprising a viewing aperture sized and shaped such that the illuminated object is visible to the user on an axis substantially perpendicular to the surface of the object, and through which ambient light, when present, also illuminates the object.

Example 4 can include, or can optionally be combined with the subject matter of one or any combination of Examples 1 through 3 to optionally include an object comprising a planar object having text.

Example 5 can include, or can optionally be combined with the subject matter of one or any combination of Examples 1 through 4 to optionally include an adjustable light source including two or more physically separated arrays of light-emitting devices.

Example 6 can include, or can optionally be combined with the subject matter of Example 5, to optionally include two or more physically separated arrays of light-emitting devices are arranged in a symmetric manner to provide uniform illumination of the object.

Example 7 can include, or can optionally be combined with the subject matter of one or any combination of Examples 1 through 6 to optionally include an adjustable light source comprising one or more arrays of light-emitting diodes (LEDs).

Example 8 can include, or can optionally be combined with the subject matter of one or any combination of Examples 1 through 7 to optionally include an adjustable light source comprising colored light-emitting diodes (LEDs), where the color property includes a hue.

Example 9 can include, or can optionally be combined with the subject matter of one or any combination of Examples 1 through 8 to optionally include an adjustable light source comprises light-emitting diodes (LEDs) having different color temperatures, and the color property includes a color temperature.

Example 10 can include, or can optionally be combined with the subject matter of Example 9, to optionally include an adjustable light source configured to establish a selected color temperature by mixing outputs from the LEDs having different color temperatures.

Example 11 can include, or can optionally be combined with the subject matter of Example 10, to optionally include colored LEDs including red and green LEDs.

Example 12 can include, or can optionally be combined with the subject matter of one or any combination of Examples 1 through 11 to optionally include user-adjustable inputs and indicators comprising independent user inputs for the calibrated illuminance and color property and corresponding indicators.

Example 13 can include, or can optionally be combined with the subject matter of one or any combination of Examples 1 through 12 to optionally include a user-adjustable input that is mechanically variable including providing a linear or rotary motion corresponding to a range of selectable values.

Example 14 can include, or can optionally be combined with the subject matter of Example 13, to optionally include an indicator comprising a calibrated scale of units aligned with the mechanically-variable user-adjustable input, where a position of the mechanically-variable user-adjustable input along the calibrated scale provides an indicium of the calibrated illuminance or color property.

Example 15 can include, or can optionally be combined with the subject matter of one or any combination of Examples 1 through 14 to optionally include a user-adjustable input coupled to the adjustable light source including inputs to receive information indicative of a selected hue and a selected tint from the user.

Example 16 can include, or can optionally be combined with the subject matter of Example 15, to optionally include an adjustable light source comprising colored light-emitting diodes (LEDs) and white LEDs, where the adjustable light source is configured to establish a specified tint using mixing of light output from the colored light emitting diodes and the white LEDs.

Example 17 can include, or can optionally be combined with the subject matter of one or any combination of Examples 15 or 16 to optionally include an object comprising a printed medium or photograph including a color image.

Example 18 can include, or can optionally be combined with the subject matter of one or any combination of Examples 1 through 17 to optionally include a housing, adjustable light source, user-adjustable input, and indicator comprising a hand-held portable assembly.

Example 19 can include, or can optionally be combined with the subject matter of one or any combination of Examples 1 through 18 to optionally include an adjustable light source configured to provide illumination of the object from an axis off-vertical.

Example 20 can include, or can optionally be combined with the subject matter of one or any combination of Examples 1 through 19 to include, subject matter (such as an apparatus, a method, a means for performing acts, or a machine readable medium including instructions that, when performed by the machine, that can cause the machine to perform acts), such as can include illuminating an object for viewing by a patient using an adjustable light source mechanically coupled to a housing, the adjustable light source coupled to a user-adjustable input, the input to obtain information from a user indicative of a calibrated illuminance and a color property to be provided by the adjustable light source including providing a range of adjustable illuminance and color properties selectable by the user, receiving information indicative of a selected illuminance and a selected color property, and using the received information, determining a lighting recommendation for presentation to the user, where the adjustable light source is configured to provide light having an illuminance in excess of 300 lux and where the housing is configured to provide a first specified distance between the adjustable light source and the object for viewing, and to obstruct viewing of the light source directly by the patient.

Example 21 can include, or can optionally be combined with the subject matter of Example 20 to optionally include a lighting recommendation comprising at least one of a recommended lighting technology, a recommended lighting distance, a recommended color property, a recommended lumen output, a recommended wattage, or a recommended lighting fixture.

Example 22 can include, or can optionally be combined with the subject matter of Example 21 to optionally include determining, using a database communicatively coupled to at least one processor circuit, a recommendation for one or more of a specific lighting product or a position of the specific lighting product with respect to an illuminated surface.

Example 23 can include, or can optionally be combined with the subject matter of one or any combination of Examples 21 through 22 to optionally include determining using a database communicatively coupled to at least one processor circuit, a recommendation for a specific lighting product, using information about at least one of the recommended lighting technology, the recommended lighting distance, the recommended color property, the recommended lumen output, the recommended wattage, or the recommended lighting fixture.

Example 24 can include, or can optionally be combined with the subject matter of Example 23 to optionally include a specific lighting product recommendation comprising information about at least one of a lighting manufacturer, a lighting vendor, a product identification, or a price.

Example 25 can include, or can optionally be combined with the subject matter of one or more of Examples 23 or 24 to optionally include a specific lighting product recommendation determined automatically at least in part using an analytical model, the analytical model including information about a distance of the lighting product from a work surface to be illuminated.

Example 26 can include, or can optionally be combined with the subject matter of one or any combination of Examples 23 or 24 to optionally include receiving an indication from a user to execute a purchase of the specific lighting product.

Example 27 can include, or can optionally be combined with the subject matter of one or any combination of Examples 23 through 26 to optionally include determining an estimate of an operating cost of the specific lighting product for presentation to a user.

Example 28 can include, or can optionally be combined with the subject matter of one or any combination of Examples 23 through 27 to optionally include receiving information indicative of the selected hue and the selected tint, and determining a tinted lens recommendation using the received information.

Example 29 can include, or can optionally be combined with the subject matter of Example 23 to optionally include providing the information indicative of the selected hue and the selected tint to a tinted lens provider for use in selecting or fabricating tinted lenses corresponding to the tinted lens recommendation.

Example 30 can include, or can optionally be combined with the subject matter of one or any combination of Examples 23 or 24 to optionally include providing the information indicative of the selected hue and the selected tint to a tinted lens provider for use in verifying that tinted lenses to be provided correspond to the tinted lens recommendation.

Example 31 can include, or can optionally be combined with the subject matter of one or any combination of Examples 1 through 30 to include, subject matter (such as an apparatus, a method, a means for performing acts, or a machine readable medium including instructions that, when performed by the machine, that can cause the machine to perform acts), such as can include a housing, an adjustable light source mechanically coupled to the housing and configured to illuminate an object for viewing by the patient on an axis substantially perpendicular to a surface of the object, a user-adjustable input coupled to the adjustable light source, the user-adjustable input configured to obtain information from a user indicative of a calibrated illuminance and a color property to be provided by the adjustable light source including providing a range of adjustable illuminance and color temperature selectable by the user, and an indicator configured to provide indicia of a selected illuminance and a selected color temperature to the user, where the adjustable light source is configured to provide light having a calibrated illuminance adjustable across a range at least including 50 lux to 5000 lux and having a calibrated color temperature adjustable across a range at least including 2700 Kelvin to 6500 Kelvin, where the housing is configured to provide a first specified distance between the adjustable light source and the object for viewing, and to obstruct viewing of the light source directly by the patient, where the adjustable light source is configured to provide illumination of the object from an axis at least 30 degrees off-vertical, and where the calibrated illuminance is established at least in part using the specified distance provided by the housing.

Example 32 can include, or can optionally be combined with the subject matter of one or any combination of Examples 1 through 30 to include, subject matter (such as an apparatus, a method, a means for performing acts, or a machine readable medium including instructions that, when performed by the machine, that can cause the machine to perform acts), such as can include or use a system to evaluate a color property for a lens for a patient by using adjustable illumination to emulate the color property of a prescribed lens, the system comprising a housing, an adjustable light source mechanically coupled to the housing and configured to illuminate an object for viewing by the patient on an axis substantially perpendicular to a surface of the object, a user-adjustable input coupled to the adjustable light source, the user-adjustable input configured to obtain information from a user indicative of a hue and a tint to be provided by the adjustable light source including providing a range of adjustable hue and tint values selectable by the user, an indicator configured to provide indicia of a selected hue and a selected tint to the user, where the adjustable light source is configured to provide light having an illuminance in excess of 300 lux, and where the housing is configured to provide a first specified distance between the adjustable light source and the object for viewing, and to obstruct viewing of the light source directly by the patient.

Example 33 can include, or can optionally be combined with the subject matter of Example 32 to optionally an adjustable light source including colored light-emitting diodes (LEDs) and white LEDs, where the adjustable light source is configured to establish a specified tint using mixing of light output from the colored light emitting diodes and the white LEDs.

Example 34 can include, or can optionally be combined with the subject matter of one or any combination of Examples 32 or 33 to optionally include an adjustable light source comprising colored light-emitting diodes (LEDs), and the hue is established by mixing light outputs from the colored LEDs.

Example 35 can include, or can optionally be combined with the subject matter of Example 34 to optionally include colored LEDs comprising red and green LEDs.

Example 36 can include, or can optionally be combined with the subject matter of one or any combination of Examples 1 through 35 to optionally include providing a selected hue and tint to a tinted lens provider for duplication of the hue and tint for use as a reference.

Example 37 can include, or can optionally be combined with the subject matter of one or any combination of Examples 1 through 36 to include, subject matter (such as an apparatus, a method, a means for performing acts, or a machine readable medium including instructions that, when performed by the machine, that can cause the machine to perform acts), such as can include quantifying traumatic brain injury comprising receiving information indicative of a preferred hue of light selected by a patient from a plurality of hues, and comparing the information indicative of the preferred hue to a reference value.

Example 38 can include, or can optionally be combined with the subject matter of Example 37 to optionally include using an illuminance of at least 200 lux.

Example 39 can include, or can optionally be combined with the subject matter of any one or more of Examples 37 or 38 to optionally include presenting the plurality of hues using a flat panel display.

Example 40 can include, or can optionally be combined with the subject matter of any one or more of Examples 37 or 38 to optionally include presenting the plurality of hues and a specified illuminance using a flat panel display.

Example 41 can include, or can optionally be combined with the subject matter of any one or more of Examples 37 or 38 to optionally include presenting the plurality of hues using a light emitting diode (LED) light source.

Example 42 can include, or can optionally be combined with the subject matter of any one or more of Examples 37 or 38 to optionally include presenting the plurality of hues and a specified illuminance using a light emitting diode (LED) light source.

Example 43 can include, or can optionally be combined with the subject matter of any one or more of Examples 37 through 42 to optionally include receiving information indicative of a preferred illuminance value of white light selected by a patient, and comparing the received information indicative of the preferred illuminance of white light to a reference value.

Example 44 can include, or can optionally be combined with the subject matter of any one or more of Examples 37 through 43 comprising selecting a light source for use by the patient using information indicative of one or more of a preferred hue or a preferred illuminance.

Example 45 can include, or can optionally be combined with the subject matter of one or any combination of Examples 1 through 44 to include, subject matter (such as an apparatus, a method, a means for performing acts, or a machine readable medium including instructions that, when performed by the machine, that can cause the machine to perform acts), such as can include simulating a filter in which an object substrate is illuminated with a light source configured to generate one or more of a hue, tint, or illuminance representing the presence of the filter without requiring use of an actual filter, and providing illumination of the object substrate with white light to present simulated comparison of viewing the object substrate without a simulated filter.

Example 46 can include, or can optionally be combined with the subject matter of Example 45 to optionally include an object substrate comprising a picture of an outdoor scene.

Example 47 can include, or can optionally be combined with the subject matter of Example 45 to optionally include an object substrate comprising a picture of an indoor scene.

Example 48 can include, or can optionally be combined with the subject matter of Example 45 to optionally include an object substrate comprising reading material.

Example 49 can include, or can optionally be combined with the subject matter of any one or more of Examples 45 through 49 to optionally include that a filter being simulated comprises a blue blocker.

Example 50 can include, or can optionally be combined with the subject matter of any one or more of Examples 45 through 49 to optionally include that a filter being simulated comprises a neutral density.

Example 51 can include, or can optionally be combined with the subject matter of any one or more of Examples 45 through 50 to optionally include that the white light has a color temperature of about 6,000° K, in order to simulate sunlight.

Example 52 can include, or can optionally be combined with the subject matter of any one or more of Examples 45 through 51 to optionally include a switch configured to receive an input from a user to toggle between a simulation of the presence of a filter and the simulation of the absence of a filter.

Example 53 can include, or can optionally be combined with the subject matter of any one or more of Examples 45 through 52 to optionally include that a filter being simulated has the effect of changing perceived color temperature and the object substrate is illuminated with a white light source having a lower color temperature and then illuminated with a white light source having a higher color temperature to simulate comparison of viewing without said filter.

Example 54 can include, or can optionally be combined with the subject matter of any one or more of Examples 45 through 53 to optionally include a system for simulating a filter, the system configured to operate according to a first mode in which a light source illuminates an object substrate with a specified hue, tint, and illuminance simulating the presence of the filter, and an input configured to receive a user input, and in response to the input, the system is configured to toggle to a second mode in which the object substrate is illuminated with white light to simulate viewing without the filter.

Example 55 can include, or can optionally be combined with the subject matter of Example 54 to optionally include that an illuminance of the source simulating the filter is adjustable, the system configured to provide an output indicative of the illuminance as a fraction of a reference value, and the white light to simulate viewing without the filter has an intensity equal to the reference value, for the purpose of simulating comparison of viewing with and without a neutral density filter.

Example 56 can include, or can optionally be combined with the subject matter of one or any combination of Examples 1 through 55 to include, subject matter (such as an apparatus, a method, a means for performing acts, or a machine readable medium including instructions that, when performed by the machine, that can cause the machine to perform acts), such as can include a system for assessing visual filters comprising an adjustable color light source, a calibration scheme established between the variable color light source and one or more tinted filters to be simulated, and one or more pictures of scenes containing objects to provide a calibrated rendering when illuminated by the variable color light source.

Example 57 can include, or can optionally be combined with the subject matter of Example 56 to optionally include that the variable color light source may be varied in one or more of the parameters of color, tint and illuminance.

Example 58 can include, or can optionally be combined with the subject matter of any one or more of Examples 56 or 57 to optionally include that the colored light source includes a red source and green source.

Example 59 can include, or can optionally be combined with the subject matter of Example 58 to optionally include a white source.

Example 60 can include, or can optionally be combined with the subject matter of any one or more of Examples 56 through 59 to optionally include that the illuminance is held constant, independent of an adjustment or one or more of a color or a tint.

Example 61 can include, or can optionally be combined with the subject matter of any one or more of Examples 56 through 60 to optionally include that the variable color light source comprises light emitting diodes.

Example 62 can include, or can optionally be combined with the subject matter of any one or more of Examples 56 through 59 to optionally include a scene comprising a hazard not observable elsewhere at the time of assessment.

Example 63 can include, or can optionally be combined with the subject matter of any one or more of Examples 56 through 62 to optionally include that the one or more filters include a blue blocker.

Example 64 can include, or can optionally be combined with the subject matter of any one or more of Examples 56 through 63 to optionally include that the one or more filters include a neutral density filter.

Example 65 can include, or can optionally be combined with the subject matter of any one or more of Examples 56 through 66 to optionally include that the scene being illuminated comprises an image having an adjusted color rendering to assist in simulation of the one or more filters.

Example 66 can include, or can optionally be combined with the subject matter of any one or more of Examples 56 through 65 to optionally include an overlay having a green or brown color for simulating green or brown tinted neutral density filters, respectively.

Example 67 can include, or can optionally be combined with the subject matter of any one or more of Examples 56 through 65 to optionally include that the one or more filters include that the scene being illuminated comprises an image having an adjusted color rendering to enhance green or brown for the purpose of simulating green or brown tinted neutral density filters, respectively.

Example 68 can include, or can optionally be combined with the subject matter of any one or more of Examples 56 through 67 to optionally include that the scene depicting the calibrated rendering includes features having differing size to assist in quantifying visual acuity in response to simulation of different filters.

Example 69 can include, or can optionally be combined with the subject matter of Example 68 to optionally include that the scene depicting the calibrated rendering includes images of potential hazards.

Example 70 can include, or can optionally be combined with the subject matter of any one or more of Examples 56 through 69 to optionally include that the scene depicting the calibrated rendering includes features having differing contrast to assist in quantifying contrast acuity in response to simulation of different filters.

Example 71 can include, or can optionally be combined with the subject matter of any one or more of examples 56 through 70 to optionally include that the scene depicting the calibrated rendering includes features having contrast that varies over different distance scales to assist in quantifying contrast acuity versus spatial frequency in response to simulation of different filters.

Example 72 can include, or can optionally be combined with the subject matter of one or any combination of Examples 1 through 71 to include, subject matter (such as an apparatus, a method, a means for performing acts, or a machine readable medium including instructions that, when performed by the machine, that can cause the machine to perform acts), such as can include assessing visual filters to improve safety comprising first selecting a picture of a scene containing a calibrated rendering of one or more objects, illuminating said scene with light having one or more of an adjustable color, and adjustable tint or an adjustable illuminance, presenting the illuminated scene to a subject, varying one or more of the color, tint, or illuminance and receiving an information indicative of preferred values with respect to the parameters of one or more of color, tint, and illuminance as indicated by the subject, and relating the preferred values to a commercially-available filter using calibration information.

Example 73 can include, or can optionally be combined with the subject matter of example 72 to optionally include that the picture is presented through a gray overlay to improve simulation of how the picture would appear as viewed through a commercially-available color filter having a shaded tone.

Example 74 can include, or can optionally be combined with the subject matter of any one or more of Examples 72 or 73 to optionally include that the evaluation of the best filter includes receiving information indicative of an ability of the subject to see features of one or more of differing contrast or differing size depicted within the picture.

Example 75 can include, or can optionally be combined with the subject matter of any one or more of Examples 72 through 74 to optionally include that the evaluation of the best filter includes receiving information indicative of an ability of the subject to see hazards depicted within the picture.

Example 76 can include, or can optionally be combined with the subject matter of any one or more of Examples 72 through 75 to optionally include using an adjustable illuminance to simulate ambient lighting conditions.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific examples in which the invention can be practiced.

These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A system for assessment of visual acuity of a patient in response to adjustable illumination of an object viewed by the patient, comprising:
    a housing;
    an adjustable light source mechanically coupled to the housing and physically arranged to illuminate the object for viewing by the patient on an axis substantially perpendicular to a surface of the object, the object comprising subject matter viewable by the patient to assess visual acuity during such viewing under various illumination conditions provided by the adjustable light source;
    a user-adjustable input coupled to the adjustable light source, the user-adjustable input providing one or more controls to obtain information from a user indicative of a calibrated illuminance and a color property to be provided by the adjustable light source including providing a range of adjustable illuminance and color properties selectable by the user to establish the various illumination conditions; and
    an indicator to provide indicia of a selected calibrated illuminance and a selected color property to the user; and
    wherein the housing provides a first specified distance between the adjustable light source and the object for viewing, and obstructs viewing of the light source directly by the patient; and
    wherein the calibrated illuminance is established at least in part using the specified distance provided by the housing.

2. The system of claim 1, wherein the calibrated illuminance and color property are independently adjustable.

3. The system of claim 1, wherein the housing includes a viewing aperture sized and shaped such that the illuminated object is visible to the user on an axis substantially perpendicular to the surface of the object, and through which ambient light, when present, also illuminates the object.

4. The system of claim 1, wherein the object includes a planar object having text.

5. The system of claim 1, wherein the adjustable light source includes two or more physically separated arrays of light-emitting devices.

6. The system of claim 5, wherein the two or more physically separated arrays of light-emitting devices are arranged in a symmetric manner to provide uniform illumination of the object.

7. The system of claim 1, wherein the adjustable light source comprises one or more arrays of light-emitting diodes (LEDs).

8. The system of claim 1, wherein the adjustable light source comprises colored light-emitting diodes (LEDs), and the color property includes a hue.

9. The system of claim 1, wherein the adjustable light source comprises light-emitting diodes (LEDs), and the color property includes a color temperature.

10. The system of claim 9, wherein the adjustable light source establishes a selected color temperature by mixing outputs from the LEDs.

11. The system of claim 10, wherein the colored LEDs include red and green LEDs.

12. The system of claim 1, wherein the user-adjustable input and indicator comprise independent user inputs for the calibrated illuminance and color property, and corresponding indicators.

13. The system of claim 1, wherein the user-adjustable input is mechanically variable including providing a linear or rotary motion corresponding to a range of selectable values.

14. The system of claim 13, wherein the indicator comprises a calibrated scale of units aligned with the mechanically-variable user-adjustable input; and
wherein a position of the mechanically-variable user-adjustable input along the calibrated scale provides an indicium of the calibrated illuminance or color property.

15. The system of claim 1, wherein the user-adjustable input coupled to the adjustable light source includes inputs to receive information indicative of a selected hue and a selected tint from the user.

16. The system of claim 15, wherein the adjustable light source includes colored light-emitting diodes (LEDs) and white LEDs; and
wherein the adjustable light source establishes a specified tint using mixing of light output from the colored light emitting diodes and the white LEDs.

17. The system of claim 15, wherein the object includes a printed medium or photograph including a color image.

18. The system of claim 1, wherein the housing, the adjustable light source, the user-adjustable input, and the indicator comprise a hand-held portable assembly.

19. The system of claim 1, wherein the adjustable light source is physically arranged to provide illumination of the object from an axis off-vertical.

20. The system of claim 1, wherein an available range of the calibrated illuminance includes a calibrated illuminance of 300 lux.

21. A non-transitory processor-readable medium, comprising instructions that, when performed by at least one processor circuit, cause a system to:
illuminate an object for viewing by a patient using an adjustable light source mechanically coupled to a housing, the adjustable light source coupled to a user-adjustable input, the input to obtain information from a user indicative of a calibrated illuminance and a color property to be provided by the adjustable light source including providing a range of adjustable illuminance and color properties selectable by the user, the object comprising subject matter viewable by the patient to assess visual acuity during such viewing under various illumination conditions provided the adjustable light source;
receive information, using a user input coupled to the at least one processor circuit, the received information indicative of a selected illuminance and a selected color property; and
using the received information, automatically determine a lighting recommendation for presentation to the user using the at least one processor circuit; and
wherein the housing provides a first specified distance between the adjustable light source and the object for viewing, and obstructs viewing of the light source directly by the patient.

22. The non-transitory processor-readable medium of claim 21, wherein the lighting recommendation comprises at least one of a recommended lighting technology, a recommended lighting distance, a recommended color property, a recommended lumen output, a recommended wattage, or a recommended lighting fixture.

23. The non-transitory processor-readable medium of claim 22, wherein the instructions include instructions to automatically determine, using a database communicatively coupled to at least one processor circuit, a recommendation for one or more of a specific lighting product or a position of the specific lighting product with respect to an illuminated surface.

24. The non-transitory processor-readable medium of claim 22, wherein the instructions include instructions to automatically determine, using a database communicatively coupled to at least one processor circuit, a recommendation for a specific lighting product, using information about at least one of the recommended lighting technology, the recommended lighting distance, the recommended color property, the recommended lumen output, the recommended wattage, or the recommended lighting fixture.

25. The non-transitory processor-readable medium of claim 24, wherein the specific lighting product recommendation includes information about at least one of a lighting manufacturer, a lighting vendor, a product identification, or a price.

26. The non-transitory processor-readable medium of claim 25, wherein the specific lighting product recommendation is determined automatically at least in part using an analytical model, the analytical model including information about a distance of the lighting product from a work surface to be illuminated.

27. The non-transitory processor-readable medium of claim 24, wherein the instructions include instructions to receive an indication from a user to execute a purchase of the specific lighting product.

28. The non-transitory processor-readable medium of claim 24, wherein the instructions include instructions to automatically determine an estimate of an operating cost of the specific lighting product for presentation to a user.

29. The non-transitory processor-readable medium of claim 24, wherein the instructions include instructions to receive information indicative of the selected hue and the selected tint, and instructions to automatically determine a tinted lens recommendation using the received information.

30. The non-transitory processor-readable medium of claim 29, wherein the instructions include instructions to provide the information indicative of the selected hue and the selected tint to a tinted lens provider for use in selecting or fabricating tinted lenses corresponding to the tinted lens recommendation.

31. The non-transitory processor-readable medium of claim 28, wherein the instructions include instructions to transmit the information indicative of the selected hue and the selected tint to a tinted lens provider for use in verifying that tinted lenses to be provided correspond to the tinted lens recommendation.

32. The non-transitory processor-readable medium of claim 21, wherein an available range of the calibrated illuminance includes a calibrated illuminance of 300 lux.

33. A system for assessment of a visual acuity of a patient in response to adjustable illumination of an object viewed by the patient, comprising:
a housing;
an adjustable light source mechanically coupled to the housing and physically arranged to illuminate the object for viewing by the patient on an axis substantially perpendicular to a surface of the object, the object comprising subject matter viewable by the patient to assess visual acuity during such viewing under various illumination conditions provided the adjustable light source;

a user-adjustable input coupled to the adjustable light source, the user-adjustable input providing one or more controls to obtain information from a user indicative of a calibrated illuminance and a color property to be provided by the adjustable light source including providing a range of adjustable illuminance and color temperature selectable by the user to establish the various illumination conditions; and an indicator to provide indicia of a selected illuminance and a selected color temperature to the user;

wherein an available range of the calibrated illuminance includes 50 lux to 5000 lux and an available calibrated color temperature includes 2700 Kelvin to 6500 Kelvin; and wherein the housing provides a first specified distance between the adjustable light source and the object for viewing, and obstructs viewing of the light source directly by the patient;

wherein the adjustable light source is physically arranged to provide illumination of the object from an axis at least 30 degrees off-vertical; and wherein the calibrated illuminance is established at least in part using the specified distance provided by the housing.

* * * * *